US008581213B2

(12) United States Patent
Kimura

(10) Patent No.: US 8,581,213 B2
(45) Date of Patent: Nov. 12, 2013

(54) BIOLOGICAL MOLECULE DETECTING APPARATUS AND BIOLOGICAL MOLECULE DETECTING METHOD

(71) Applicant: FUJIFILM Corporation, Tokyo (JP)

(72) Inventor: Toshihito Kimura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/854,266

(22) Filed: Apr. 1, 2013

(65) Prior Publication Data

US 2013/0217035 A1    Aug. 22, 2013

Related U.S. Application Data

(63) Continuation of application No. PCT/JP2011/005490, filed on Sep. 29, 2011.

(30) Foreign Application Priority Data

Sep. 30, 2010   (JP) .................................. 2010-222937
May 24, 2011    (JP) ................................... 2011-115474

(51) Int. Cl.
*G01N 21/64*         (2006.01)
(52) U.S. Cl.
USPC .................... 250/461.2; 250/458.1; 250/459.1
(58) Field of Classification Search
USPC ....................................................... 250/461.2
See application file for complete search history.

(56) References Cited

U.S. PATENT DOCUMENTS

| 4,902,630 | A | * | 2/1990 | Bennett et al. ................. 436/546 |
| 5,166,052 | A | * | 11/1992 | Cercek et al. ................ 435/7.24 |
| 5,302,349 | A | * | 4/1994 | Dandliker et al. .......... 422/82.08 |
| 5,811,312 | A | * | 9/1998 | Hasegawa et al. ............ 436/527 |
| 6,448,018 | B1 | * | 9/2002 | Nakayama et al. ............ 435/7.1 |

(Continued)

FOREIGN PATENT DOCUMENTS

| JP | 61-272637 A | 12/1986 |
| JP | 62-38346 A | 2/1987 |

(Continued)

OTHER PUBLICATIONS

International Preliminary Report on Patentability; PCT/JP2011/005490; Apr. 9, 2013.

(Continued)

*Primary Examiner* — David Porta
*Assistant Examiner* — Djura Malevic
(74) *Attorney, Agent, or Firm* — Sughrue Mion, PLLC

(57) ABSTRACT

A configuration was adopted, in which the orientations of free molecules and binding molecules within a solution are switched by switching the vibration direction of orientation controlling light, thereby switching the amount of light emitted by each free molecule and each binding molecule. There is a difference in the amounts of time required for the orientations of the free molecules and the binding molecules to switch accompanying the switch in the emission direction of the orientation controlling light. Therefore, the timings at which the amounts of light emitted by each type of molecule increase differ. Accordingly, the fluorescence contributed by fluorescent molecules associated with free molecules and the fluorescent molecules associated with binding molecules can be respectively calculated, even if all of the fluorescent molecules within the solution emit fluorescence. Thereby, the concentration of a detection target substance can be accurately measured with a simple structure.

17 Claims, 28 Drawing Sheets

(56) References Cited

U.S. PATENT DOCUMENTS

| | | | |
|---|---|---|---|
| 6,455,861 B1* | 9/2002 | Hoyt | 250/458.1 |
| 6,667,830 B1* | 12/2003 | Iketaki et al. | 359/368 |
| 6,914,720 B2* | 7/2005 | Tahara et al. | 359/368 |
| 6,992,761 B2* | 1/2006 | Modlin et al. | 356/317 |
| 2004/0239854 A1 | 12/2004 | Monobe et al. | |
| 2005/0221271 A1 | 10/2005 | Murphy et al. | |
| 2006/0109546 A1 | 5/2006 | Namba et al. | |
| 2011/0140000 A1* | 6/2011 | Iketaki | 250/458.1 |

FOREIGN PATENT DOCUMENTS

| | | |
|---|---|---|
| JP | 7-120397 A | 5/1995 |
| JP | 2000-19172 A | 1/2000 |
| JP | 2003-315258 A | 11/2003 |
| JP | 2005-17282 A | 1/2005 |
| JP | 2006-501860 A | 1/2006 |
| JP | 2008-298743 A | 12/2008 |
| WO | 03/024586 A1 | 3/2003 |

OTHER PUBLICATIONS

Tina L. Mann et al., "Fluorescence polarization spectroscopy in protein analysis", Analyst, 2003, pp. 313-317, vol. 128.

Kazuaki Nagayama et al., "Three-dimensional morphological analysis of mechanical response of MC3T3-E1 osteoblast-like cells cultured in collagen gel", Proceedings of the Bioengineering Conference annual meeting of BED/JSME, 2007, No. 06-65, pp. 110-111.

International Search Report for PCT/JP2011/005490 dated Dec. 27, 2011.

* cited by examiner

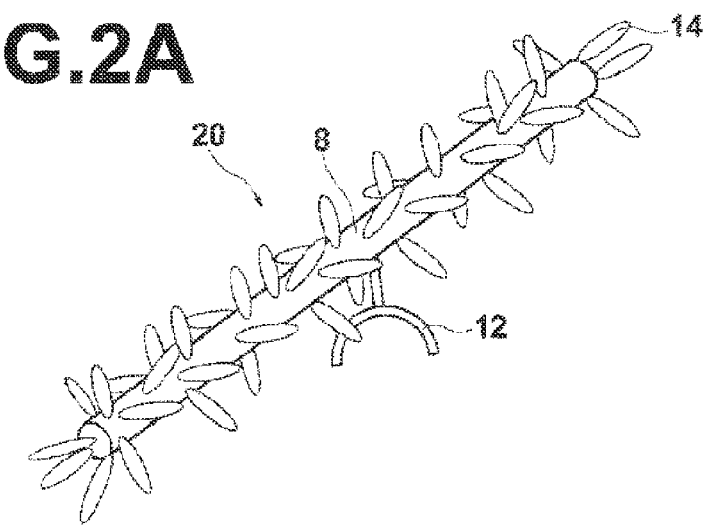
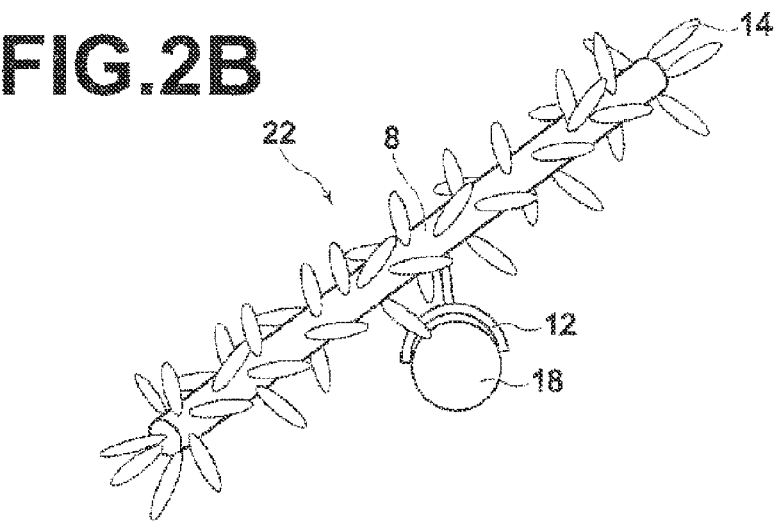

FIG.3A
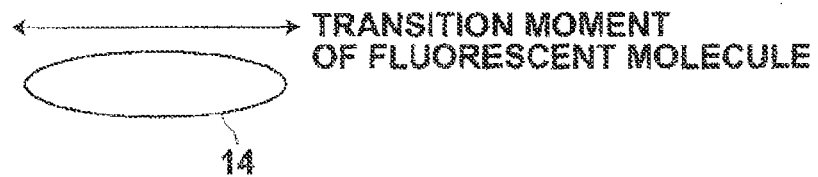
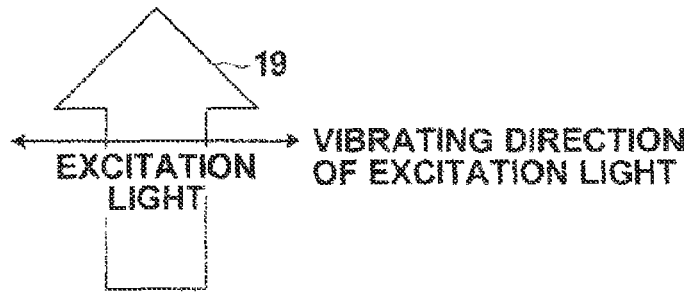
FIG.3B
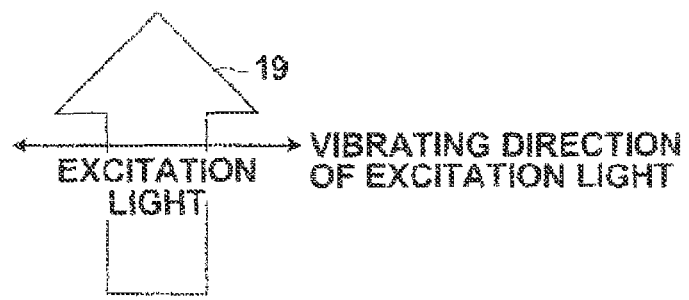

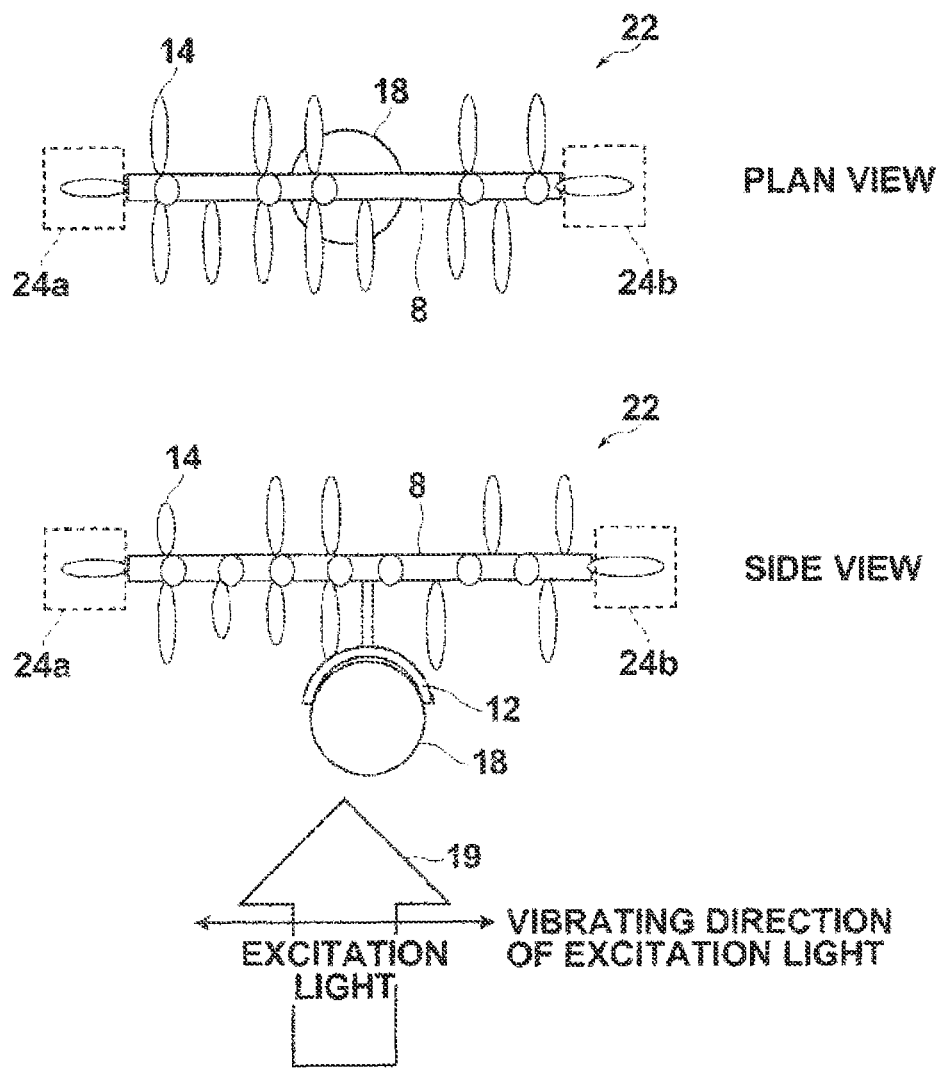

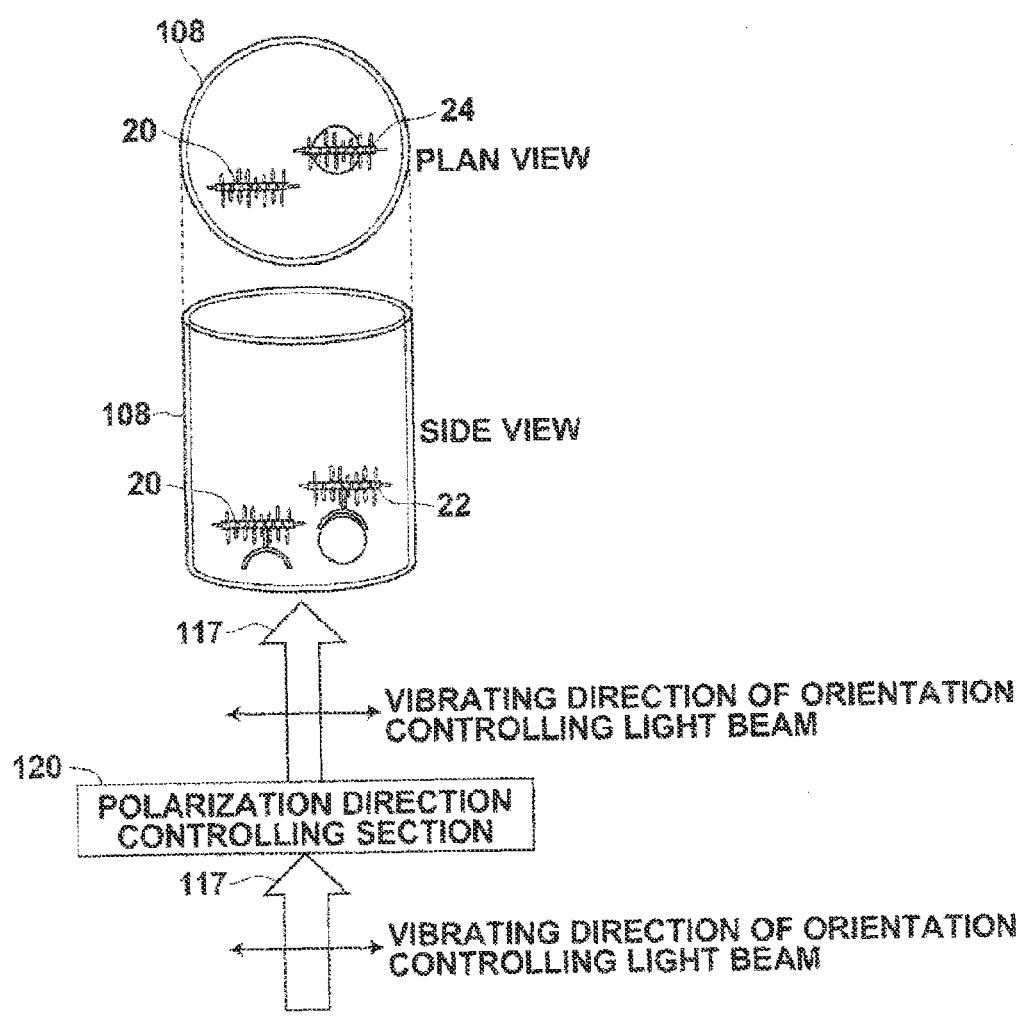

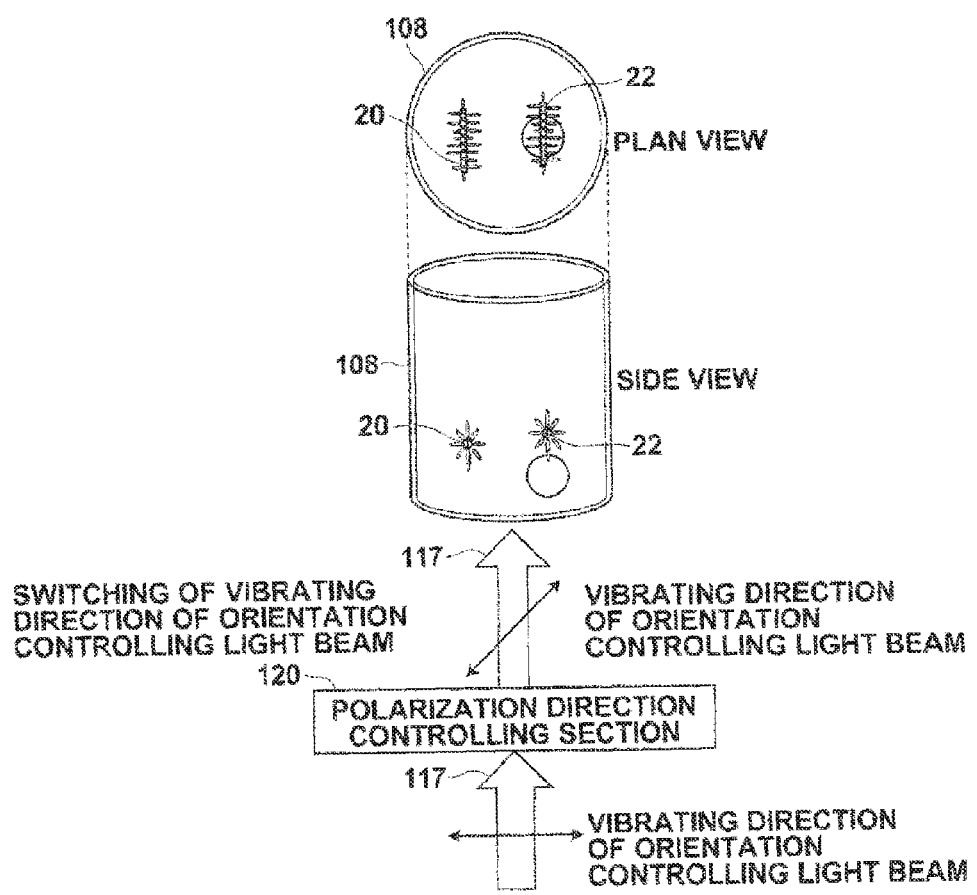

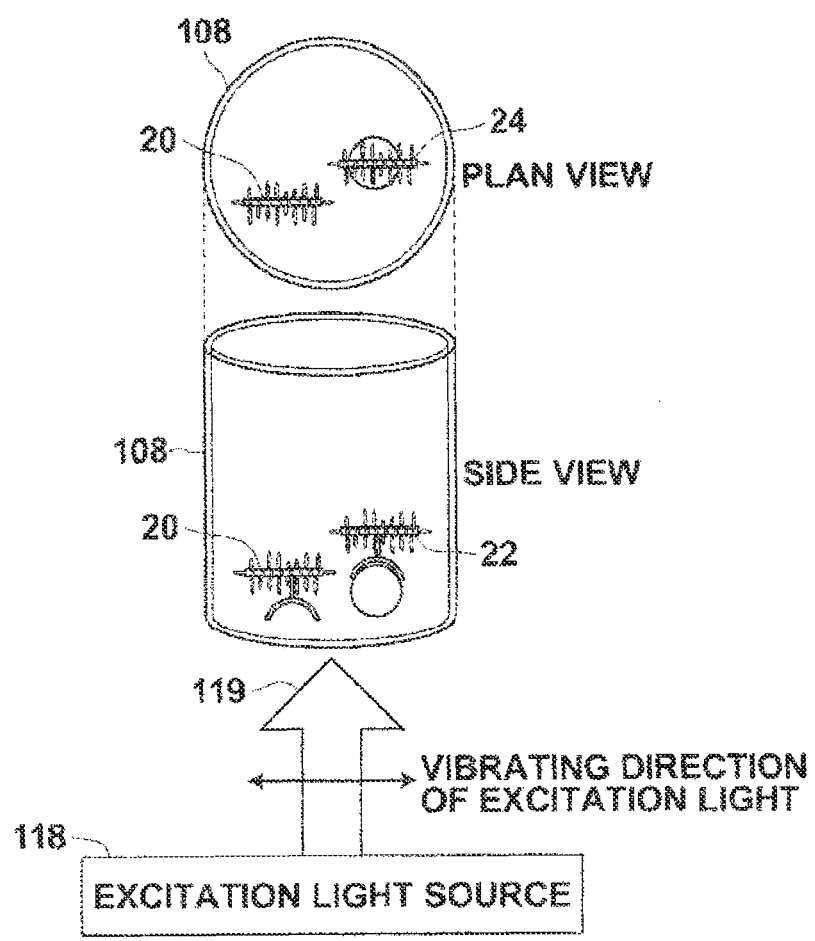

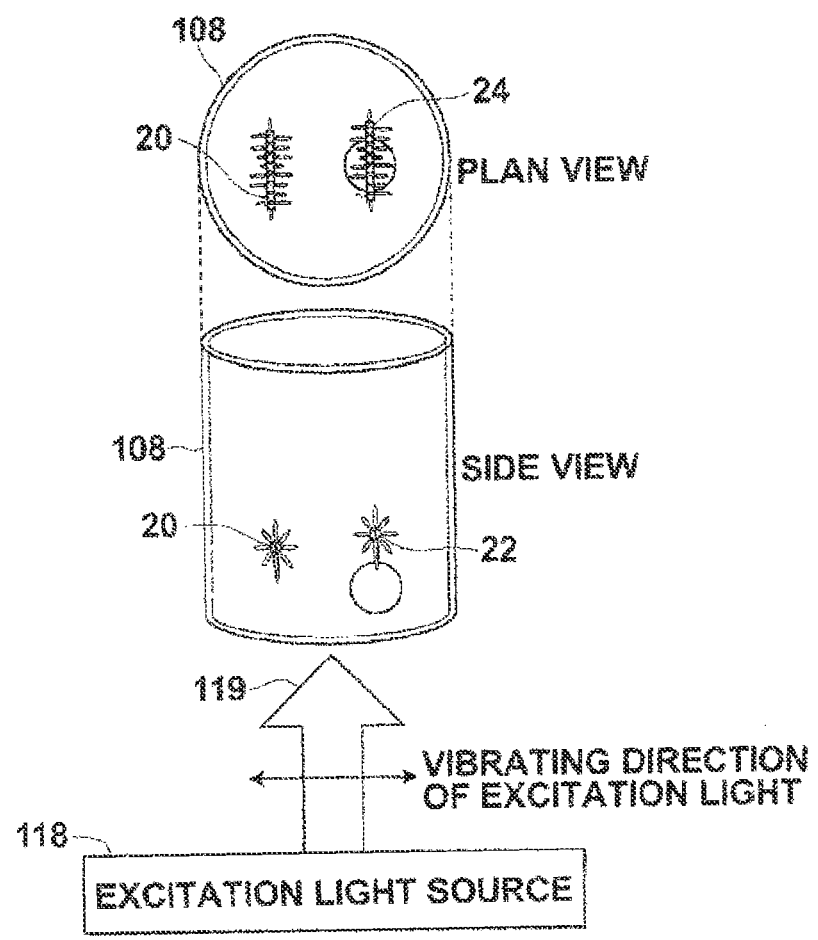

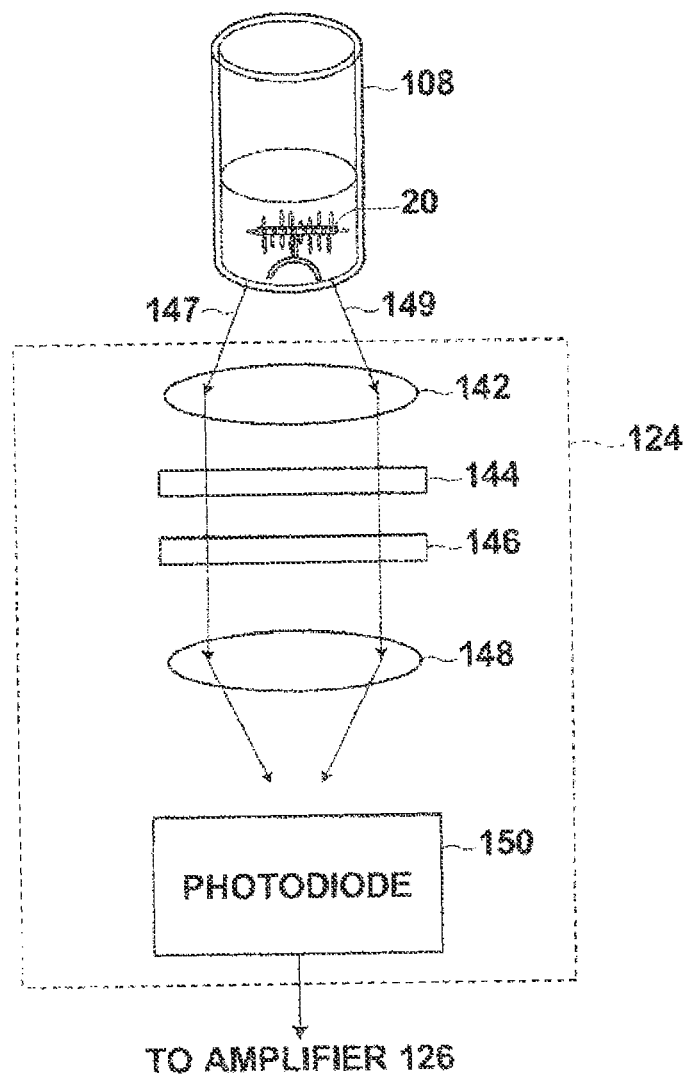

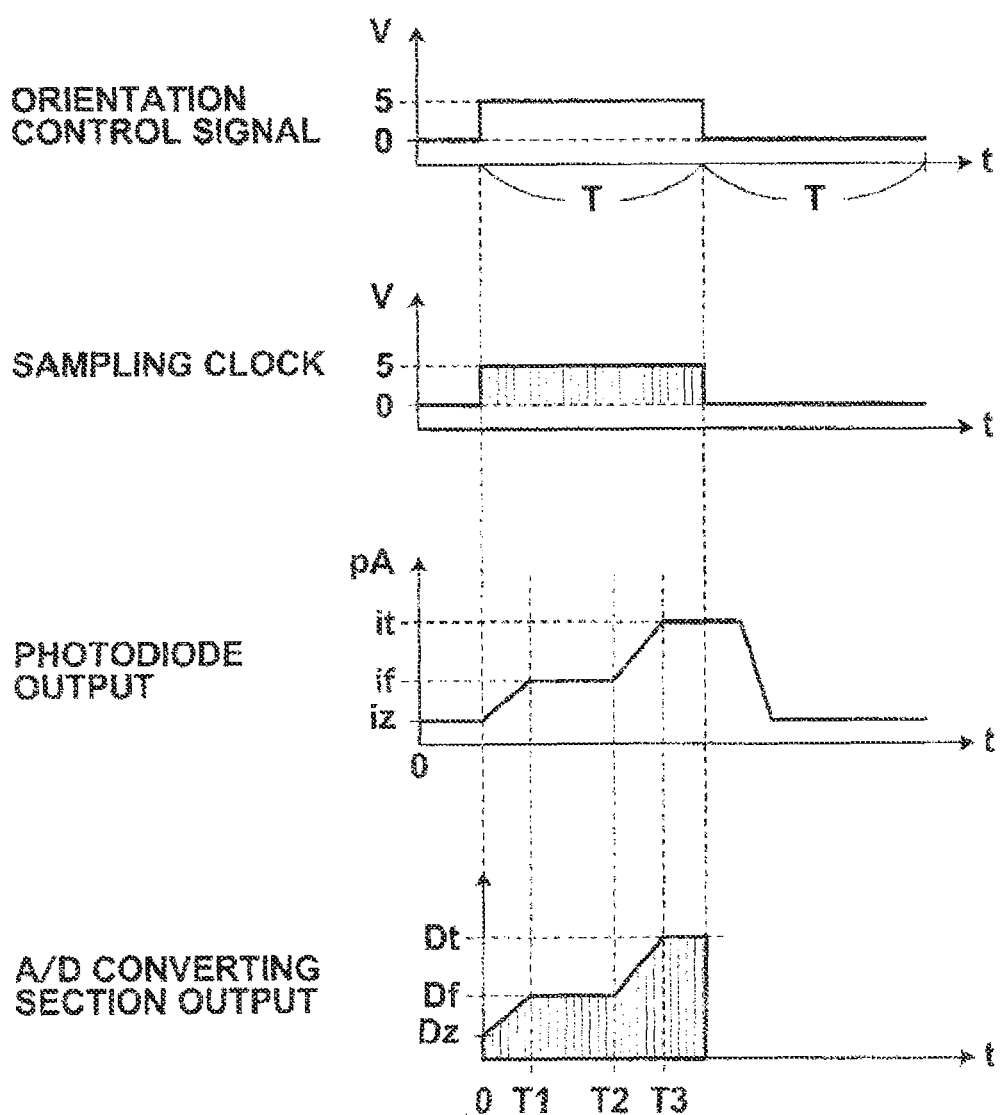

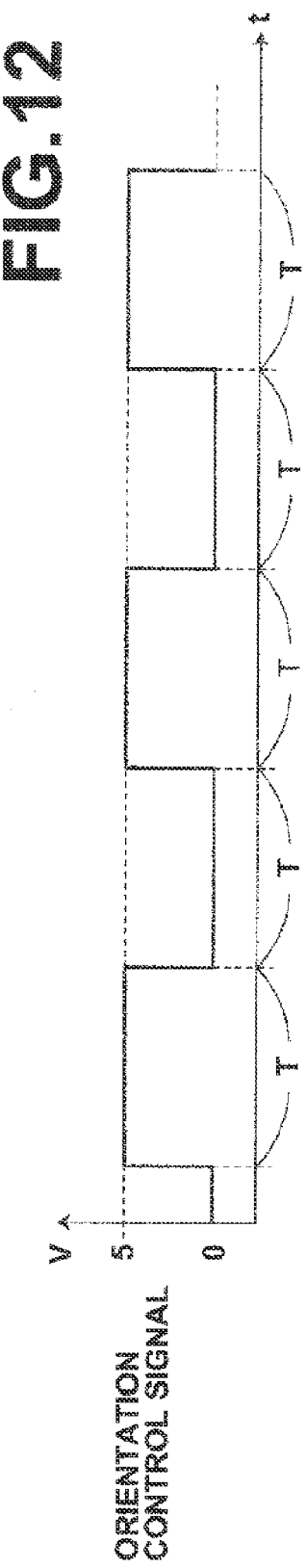

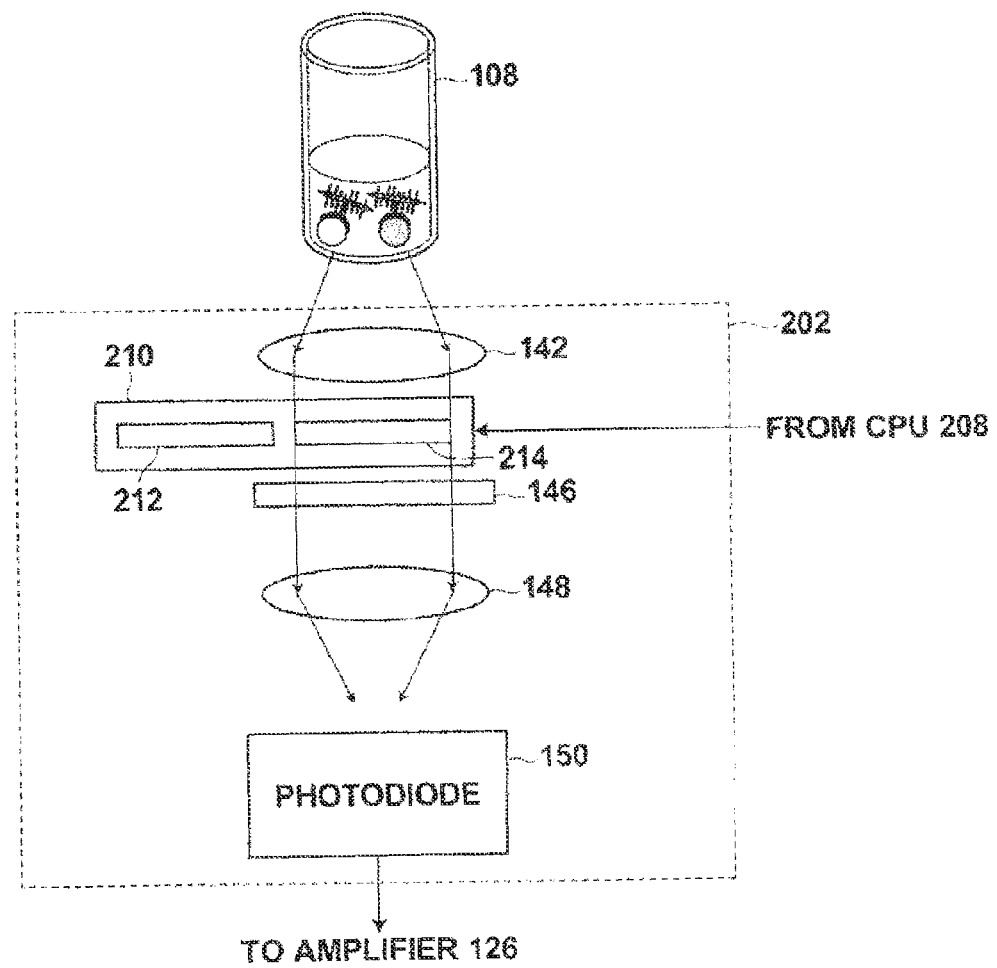

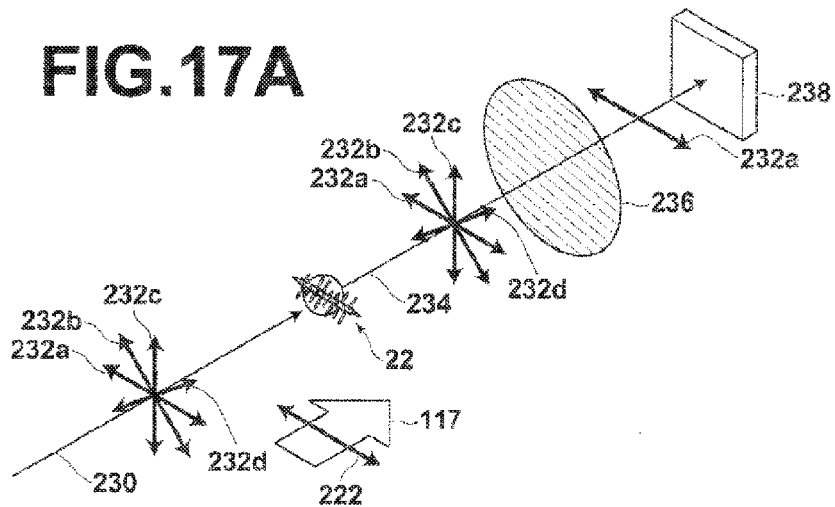
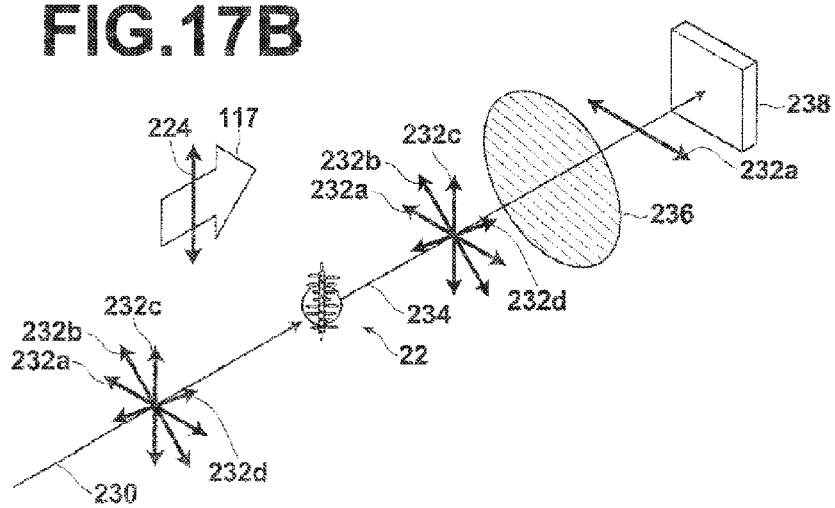

FIG.19
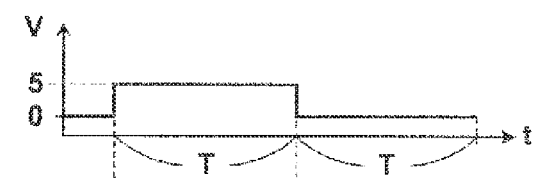
ORIENTATION CONTROL SIGNAL
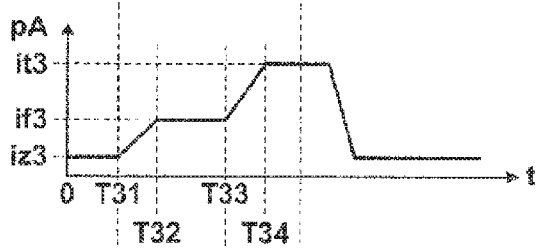
OUTPUT OF PHOTODIODE THAT RECEIVES LIGHT TRANSMITTED THROUGH POLARIZING BEAM SPLITTER
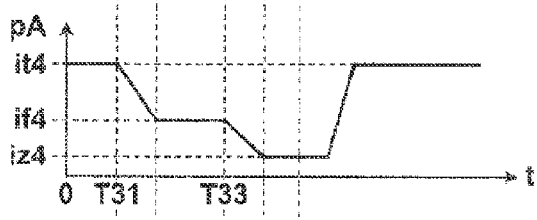
OUTPUT OF PHOTODIODE THAT RECEIVES LIGHT REFLECTED BY POLARIZING BEAM SPLITTER
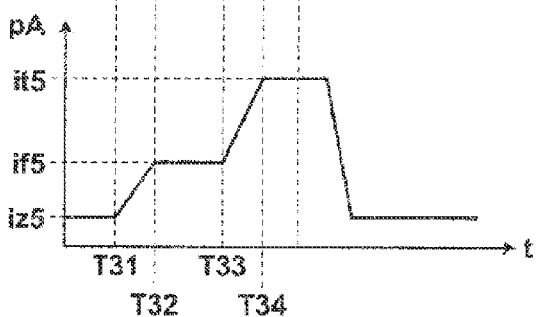
NORMALIZED PHOTODIODE OUTPUT

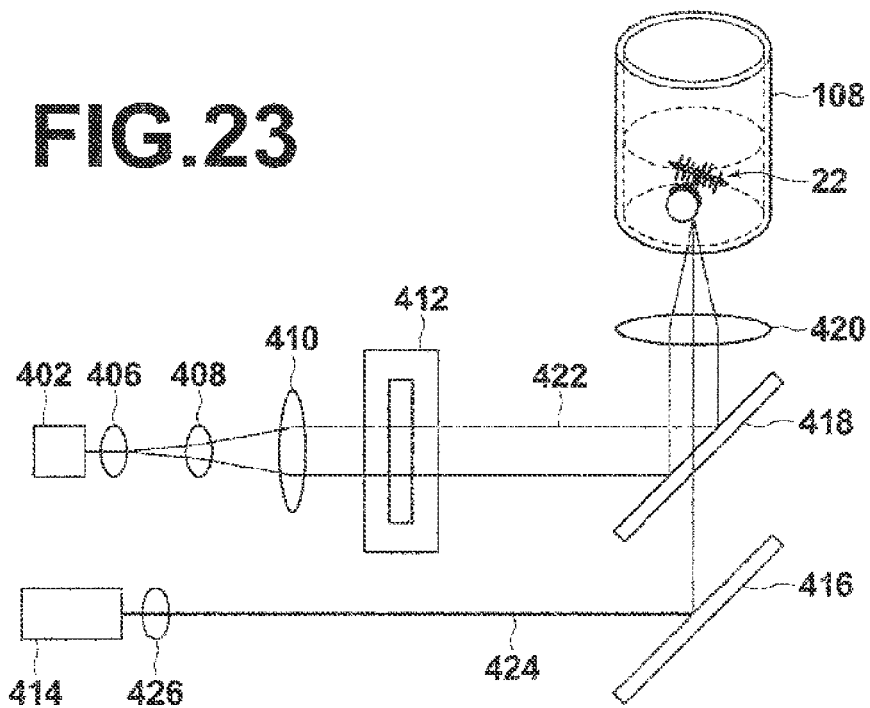
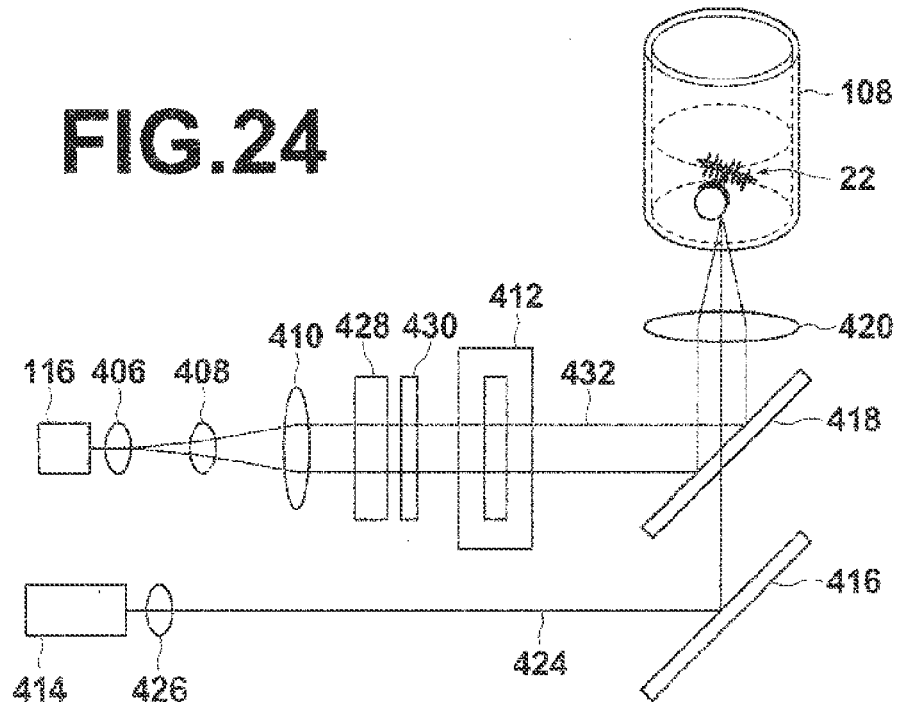

BIOLOGICAL MOLECULE DETECTING APPARATUS AND BIOLOGICAL MOLECULE DETECTING METHOD

TECHNICAL FIELD

The present invention is related to technology for detecting detection target substances within solutions. Particularly, the present invention is related to a biological molecule detecting apparatus and a biological molecule detecting method capable of detecting biological molecules, viruses, nucleic acids, proteins, and germs within samples.

BACKGROUND ART

Recently, biological molecule detecting methods, in which physicians or technicians detect biological molecules at points of care, immediately obtain measurement results, and utilize the measurement results for diagnosis and treatment, are being focused on. Biological molecule detecting methods are methods for selectively detecting only detection target substances from within bodily fluids such as blood, urine, and sweat, by the high selectivity of specific reactions such as antigen antibody reactions. Such biological molecule detecting methods are particularly widely employed to detect, inspect, quantify, and analyze small amounts of biological molecules, such as viruses, nucleic acids, proteins, and germs.

Radioimmunoassay is a biological molecule detecting method which is in practical use. Radioimmunoassay employs antigens or antibodies labeled with isotopes, and detects the presence of antibodies or antigens that specifically bind with the labeled antigens or the labeled antibodies.

Fluorescence immunoassay is a biological molecule detecting method that does not employ radioactive substances. Fluorescence immunoassay apparatuses, in which antibodies are immobilized onto a reaction layer in advance (referred to as a solid phase), a measurement target solution and antibodies labeled with fluorescent molecules are caused to flow onto the reaction layer, and fluorescence in the vicinity of the reaction layer is observed to measure the concentration of antigens which have specifically bound to the antibodies, are known (refer to Japanese Unexamined Patent Publication No. 7 (1995)-120397, for example).

However, fluorescence immunoassay that utilizes solid phases has a problem that it is costly to produce the solid phases. There is a method that utilizes fluorescence polarization method to confirm antigen antibody reactions in solutions (referred to as a liquid phase) as a method that does not employ solid phases. The fluorescence polarization method is a method that detects changes in degrees of fluorescence polarization caused by changes in Brownian motion that occurs by the sizes of molecules changing by molecules binding with molecules which have fluorescent labels. The biological molecule detecting method that utilizes the fluorescence polarization method is known as a simple and expedient method for detecting detection target substances within samples (refer to Japanese Unexamined Patent Publication No. 2008-298743, for example).

DISCLOSURE OF THE INVENTION

However, the conventional fluorescence polarization method utilizes changes in Brownian motion, which is random, and therefore has a problem that there is a limit to measurement sensitivity. In addition, the method disclosed in Japanese Unexamined Patent Publication No. 2008-298743 requires that fluorescent lifetimes are long enough to be influenced by changes in Brownian motion. However, fluorescence lifetimes are influenced by components within samples. Therefore, there are cases in which fluctuations will occur in the measurement results obtained by the method of Japanese Unexamined Patent Publication No. 2008-298743.

The present invention has been developed in view of the foregoing circumstances. It is an object of the present invention to provide a biological molecule detecting apparatus and a biological molecule detecting method which are capable of highly sensitive measurements.

A biological molecule detecting method of the present invention that achieves the above object comprises the steps of:

emitting excitation light, having a linearly polarized component polarized in a specific direction, to excite fluorescent molecules within a solution;

detecting first fluorescence emitted by a first complex constituted by a substance that specifically binds with a detection target substance, an orienting label, and a plurality of the fluorescent molecules which are bound to the periphery of the orienting label;

detecting second fluorescence emitted by a second complex constituted by the first complex which is bound to the detection target substance;

switching the orientations of the first complex and the second complex in at least two directions;

detecting or quantifying the detection target substance based on the detected first fluorescence and the detected second fluorescence.

A biological molecule detecting apparatus of the present invention comprises:

a light source that emits the excitation light having the component which is linearly polarized in a specific direction that excites the fluorescent molecules;

a light receiving section that detects the fluorescence emitted by the fluorescent molecules;

orientation control means for switching the orientations of the first complex and the second complex within the solution in at least two directions; and a calculating section that detects or quantifies the detection target substance by calculating the intensity of the second fluorescence from temporal changes in the intensity of the fluorescence emitted by the fluorescent molecules accompanying the switching of the orientations of the first complex and the second complex.

It is preferable for the biological molecule detecting apparatus of the present invention to adopt a configuration, wherein:

the orientation control means switches the orientation of the first complex and the second complex between an orientation in a first direction in which the longitudinal directions of the orienting labels and the specific are parallel, and an orientation in a second direction in which the longitudinal direction of the orienting labels and the specific direction are perpendicular.

It is preferable for the biological molecule detecting apparatus of the present invention to adopt a configuration, wherein:

the orientation control means switches the orientation of the first complex and the second complex at predetermined temporal intervals; and the calculating section calculates an arithmetic mean of a plurality of intensities of the second fluorescence, obtained by the orientations of the first complex and the second complex being switched a plurality of times, and detects or quantifies the detection target substance based on the arithmetic mean of the fluorescent intensities.

It is preferable for the biological molecule detecting apparatus of the present invention to adopt a configuration, wherein:

the predetermined temporal intervals are determined based on one of the mass and the volume of the detection target substance, one of the mass and the volume of the specific binding substance, one of the mass and volume of the orienting label, one of the mass and the volume of the fluorescent molecules, and the intensity of orientation control exerted by the orientation control means.

It is preferable for the biological molecule detecting apparatus of the present invention to adopt a configuration, wherein:

the orientation control means is equipped with an orientation controlling light source that emits linearly polarized light, and controls the orientations of the first complex and the second complex by emitting the linearly polarized light onto the solution.

It is preferable for the biological molecule detecting apparatus of the present invention to adopt a configuration, wherein:

the orientation control means is equipped with a wavelength plate that changes the vibration direction of the linearly polarized light, and switches the orientations of the first complex and the second complex by switching the vibration direction of the linearly polarized light employing the wavelength plate.

It is preferable for the biological molecule detecting apparatus of the present invention to adopt a configuration, wherein:

the orientation controlling light source emits the linearly polarized light onto the solution from a plurality of positions.

It is preferable for the biological molecule detecting apparatus of the present invention to adopt a configuration, wherein:

the solution is held in a solution holding portion having a flat surface at least at a portion thereof.

It is preferable for the biological molecule detecting apparatus of the present invention to adopt a configuration, wherein:

the orientation controlling light source emits the linearly polarized light in a direction that passes through the solution and exits the flat surface of the solution holding portion such that the linearly polarized light is focused at an interface between the solution and the flat surface.

It is preferable for the biological molecule detecting apparatus of the present invention to adopt a configuration, wherein:

the calculating section calculates the intensity of the second fluorescence by utilizing the fact that there are differences in the temporal changes in the intensity of fluorescence emitted by the first complex and the temporal changes in the intensity of fluorescence emitted by the second complex during the switch of the orientation by the orientation control means from a first direction to a second direction.

It is preferable for the biological molecule detecting apparatus of the present invention to adopt a configuration, wherein:

the light receiving section is equipped with spectral means for spectrally separating light.

It is preferable for the biological molecule detecting apparatus of the present invention to adopt a configuration, wherein:

the spectral means is a plurality of filters having different properties; and the light receiving section switches a filter to be employed from among the plurality of filters according to the wavelength of the fluorescence emitted by the fluorescent molecules.

The present invention enables highly sensitive detection of biological molecules.

BRIEF DESCRIPTION OF THE DRAWINGS

FIG. 2A is a schematic diagram that illustrates a free molecule (an antibody and a fluorescent molecule to which an antigen is not bound).

FIG. 2B is a schematic diagram that illustrates a binding molecule (an antibody and a fluorescent molecule to which an antigen is bound).

FIG. 3A is a schematic diagram that illustrates a case in which the vibration direction of excitation light and the transition moment of a fluorescent molecule are parallel.

FIG. 3B is a schematic diagram that illustrates a case in which the vibration direction of excitation light and the transition moment of a fluorescent molecule are perpendicular.

FIG. 4A is a diagram that illustrates a case in which the vibration direction of excitation light and the longitudinal direction of an orienting label are parallel.

FIG. 7A is a collection of diagrams that illustrates the relationship between the vibration direction of an orientation controlling light beam and the orientations of a free molecule and a binding molecule.

FIG. 7C is a collection of diagrams that illustrates a state in which reorientation of a free molecule and a binding molecule is completed after the vibration direction of an orientation controlling light beam is switched.

FIG. 8A is a diagram that illustrates the relationship between an oriented free molecule and an oriented binding molecule and the vibration direction of excitation light.

FIG. 8B is a diagram that illustrates the relationship between a free molecule and a binding molecule oriented in a different direction and the vibration direction of excitation light.

FIG. 9 is a schematic diagram that illustrates the detailed structure of a light receiving section of the biological molecule detecting apparatus according to the first embodiment.

FIG. 11 is a collection of graphs that illustrate an orientation control signal, a sampling clock, PD output, and A/D converting section output for a single cycle in the biological molecule detecting apparatus according to the first embodiment.

FIG. 12 is a graph that illustrates orientation control signals for a plurality of cycles in the biological molecule detecting apparatus according to the first embodiment.

FIG. 15 is a schematic diagram that illustrates the detailed structure of a light receiving section of the biological molecule detecting apparatus according to the second embodiment.

FIG. 17A is a conceptual diagram that illustrates the relationship between the transition moment of a fluorescent molecule and the vibration direction of randomly polarized excitation light in the case that a laser beam is emitted from a first direction.

FIG. 17B is a conceptual diagram that illustrates the relationship between the transition moment of a fluorescent molecule and the vibration direction of randomly polarized excitation light in the case that a laser beam is emitted from a second direction.

FIG. 19 is a collection of graphs that illustrate the changes in the output of photodiodes accompanying changes in the direction of the transition moment of a fluorescent molecule.

FIG. 23 is a conceptual diagram that illustrates an example of the structure of an optical system for casing linearly polarized laser beams to be emitted onto a plurality of points from a predetermined direction.

FIG. 24 is a conceptual diagram that illustrates another example of the structure of an optical system for casing linearly polarized laser beams to be emitted onto a plurality of points from a predetermined direction.

BEST MODE FOR CARRYING OUT THE INVENTION

Hereinafter, embodiments of the present invention will be described with reference to the attached drawings. Various specific reactions are utilized to detect biological molecules. Here, apparatuses that utilize specific reactions between antigens and antibodies, and detect antigens which have reacted with the antibodies, based on fluorescence emitted by fluorescent molecules which are bound to the antibodies as labels, will be described as examples.

First Embodiment

Figure 1A:
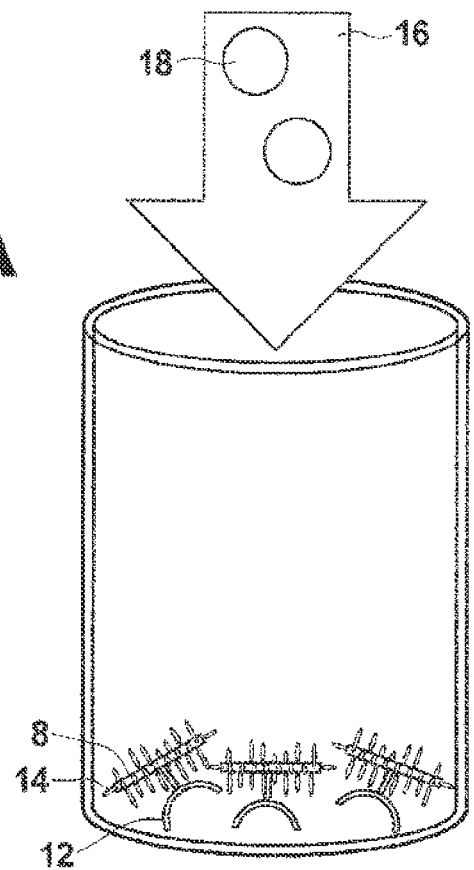
FIG. 1A is a first schematic diagram that illustrates antigen antibody reactions in a biological molecule detecting apparatus according to a first embodiment.
Figure 1B:
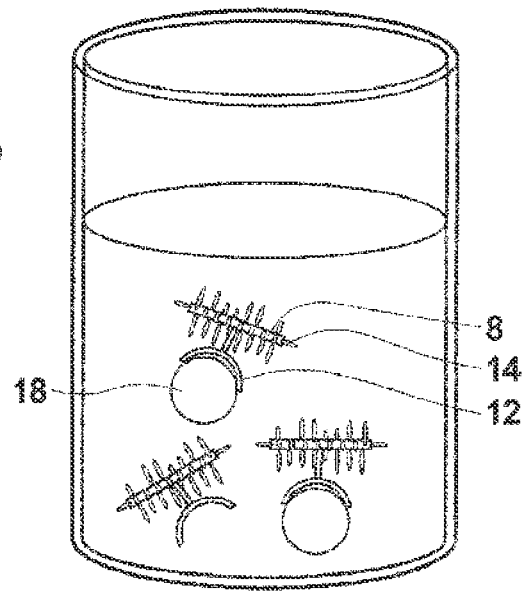
FIG. 1B is a second schematic diagram that illustrates antigen antibody reactions in the biological molecule detecting apparatus according to the first embodiment.

FIG. 1A and FIG. 1B are schematic diagrams that illustrate antigen antibody reactions in a biological molecule detecting apparatus according to a first embodiment. Antigen antibody reactions within a liquid will be described with reference to FIG. 1A and FIG. 1B. The first embodiment utilizes a single type of antibody and detects a single type of antigen within a uniform solution. Here, a case will be considered in which dried antibodies 12 are contained in a cylindrical reagent cup 10. The antibodies 12 are bound to cylindrically shaped orienting labels 8. A plurality of fluorescent molecules 14 are fixed about the peripheries of the orienting labels 8.

In the present embodiment, plasma 16 separated from whole blood is the sample from which biological molecules are detected. The plasma 16 is dispensed into the reagent cup 10 and stirred. In the case that antigens 18 that specifically bind with the antibodies 12 are present in the plasma 16, antigen antibody reactions will occur between the antibodies 12 and the antigens 18, and the antibodies 12 and the antigens 18 will be present within the plasma 16 in a specifically bound state, as illustrated in FIG. 1B. A sufficiently great amount of the antibodies 12 is supplied with respect to the antigens 18. Therefore, a portion of the antibodies 12 remain within the plasma 16 without undergoing antigen antibody reactions. Hereinafter, the antibodies 12, the antigens 18, the orienting labels 8, and the fluorescent molecules 14 which are bound to each other by antigen antibody reactions will be referred to as binding molecules, and the antibodies 12, the orienting labels 8, and the fluorescent molecules 14 which have not undergone antigen antibody reactions will be referred to as free molecules. The binding molecules and the free molecules are both present in the plasma. Note that components other than the antigens 18 are present in the plasma. However, components other than the antigens 18 are omitted from FIG. 1A and FIG. 1B in order to simplify the description.

The biological molecule detecting apparatus according to the first embodiment of the present invention emits excitation light into the solution, in which the binding molecules and the free molecules are both present, as the solution is a liquid phase. Fluorescence emitted by the fluorescent molecules 14 associated with the free molecules and the binding molecules is received, and detection and quantification of the antigens 18 is performed based on the received fluorescence. Accordingly, it is desirable for only fluorescence emitted from the binding molecules that include the antigens 18 to be detected. However, the free molecules and the binding molecules are both present in the solution. Therefore, when the excitation light is emitted into the solution, the fluorescent molecules 14 associated with the free molecules also emit fluorescence, resulting in unnecessary fluorescent components being generated. Therefore, the biological molecule detecting apparatus according to the first embodiment of the present invention detects the fluorescence while switching the orientations of the free molecules and the binding molecules, and calculates the fluorescence contributed by fluorescent molecules associated with free molecules from among the entirety of the fluorescence data based on changes in the intensity of fluorescence accompanying the switches in orientations.

The structures of the free molecules and the binding molecules will be described with reference to FIGS. 2A and 2B in order to explain the principle of calculating the fluorescence contributed by the binding molecules and the fluorescence contributed by the free molecules in the biological molecule detecting apparatus according to the first embodiment of the present invention. FIG. 2A is a schematic diagram that illustrates a free molecule 20. The free molecule 20 has an antibody 12, an orienting label 8, and fluorescent molecules 14. FIG. 2B is a schematic diagram that illustrates a binding molecule 22. The binding molecule 22 has an antibody 12, an orienting label 8, fluorescent molecules 14, and an antigen 18 which is bound to the antibody 12.

The orienting label 8 is a label that binds with the antibody 12 and the fluorescent molecules 14, and orients the antibody 12 and the fluorescent molecules 14. The orienting label 8 is shaped as an elongated rod, and has properties of becoming oriented in specific directions when it receives external force in the form of light. The antibody 12 and the fluorescent molecules 14 also attempt to become oriented in specific directions by receiving external force from light, but there are cases in which they cannot be oriented in the case that the molecular weights thereof are too small. Therefore, the orienting label 8 is bound to the antibody 12 and the fluorescent molecules 14 in the present embodiment, and the antibody 12 and the fluorescent molecules 14 are caused to be oriented by orienting the orienting label 8. For example, an I type collagen having a length of approximately 300 nm in the longitudinal direction thereof may be employed as the orienting label 8. The orienting label 8 is sufficiently larger than the antibody 12 and the fluorescent molecules 14. Note that the orienting label 8 is illustrated as being of a cylindrical shape in FIG. 2A and FIG. 2B in order to facilitate understanding of the explanation. Arbitrary known methods may be employed to bind collagen with the antibodies 12 or with the fluorescent molecules 14.

The fluorescent molecules 14 are molecules that emit fluorescence in response to receiving excitation light. The fluorescent molecules 14 are bound to both end surfaces of the orienting label 8 and bound evenly in a radial manner to the lateral surface of the orienting label 8.

The antibody 12 is a substance that specifically binds to the antigen 18, and is bound to the orienting label 8. A substance that specifically binds to a detection target substance that users wish to detect is utilized is utilized as the antibody 12.

In the present embodiment, a case will be described in which whole blood is employed as the sample, PSA (Prostate Specific Antigens) are the antigens 18 as the detection target substance, and anti PSA antibodies are employed as the antibodies 12 that specifically bind with the detection target substance. Alexa Fluor 568 (by Molecular Probes) is employed as the fluorescent molecules 14. Alexa Fluor 568 emits fluorescence having wavelengths within a range from 550 nm to 700 nm, with a peak at approximately 610 nm.

The size of the fluorescent molecules 14 (Alexa Fluor 568) is approximately 1 nm. Accordingly, the fluorescent molecules 14 are sufficiently smaller than the orienting label 8, and a plurality of the fluorescent molecules 14 can be caused to bind to the periphery of the orienting label 8. Note that in FIGS. 2A and 2B, the fluorescent molecules 14 are illustrated larger than their actual size in order to facilitate understanding of the explanation.

The fluorescent molecules 14 transition to an excited state when light energy is absorbed, and emits fluorescence during the process of returning to a baseline state. The fluorescent molecules 14 transition to an excited state when light energy is absorbed, and emits fluorescence during the process of returning to a baseline state. When a fluorescent molecule 14 is excited by linearly polarized excitation light, the fluorescent molecule 14 emits fluorescence which is polarized in the same direction as the vibration direction of the excitation light. The degree of polarization of fluorescence emitted by the fluorescent molecules 14 depends on the speed of rotational movement thereof. That is, if a fluorescent molecule 14 is not undergoing rotational movement, the fluorescent molecule 14 emits fluorescence which is polarized in the same direction as the vibration direction of the excitation light. The degree of polarization of the fluorescence emitted by fluorescent molecules 14 decreases as the speed at which they are undergoing rotational movement becomes greater. Note that in the present specification, the "vibration direction" of light refers to the vibrating direction of an electric field, which is the same direction as a polarization direction in the case that light is polarized.

When the fluorescent molecules 14 are excited, vectors within the fluorescent molecules called transition moments, which are determined by the molecular structures of the fluorescent molecules 14, interact with the excitation light. The transition moments have unique directions within the fluorescent molecules 14, and the relationship between the directions of the transition moments and the vibration direction of the excitation light determines the excitation efficiency of the fluorescent molecules 14. Specifically, the fluorescent molecules 14 selectively absorb light that vibrates in a direction parallel to the transition moments thereof. Accordingly, in the case that the excitation light 19 is emitted onto a fluorescent molecule 14 while vibrating in the vertical direction of the drawing sheet and propagating from the left to the right of the drawing sheet as illustrated in FIGS. 3A and 3B, the excitation efficiency becomes greatest in the case that the vibration direction of the linearly polarized excitation light 19 is parallel to the transition moment of the fluorescent molecule 14 (FIG. 3A), decreases as the angle formed by the vibration direction of the linearly polarized excitation light 19 increases, and becomes 0 in the case that the vibration direction of the linearly polarized excitation light 19 is perpendicular to the transition moment of the fluorescent molecule 14 (FIG. 3B). The orientations of the transition moments change according to the orientations of the fluorescent molecules 14, and therefore the orientations of the fluorescent molecules 14 within the solution influence the excitation efficiencies thereof. Note that here, cases have been illustrated in which the longitudinal directions of the fluorescent molecules 14 and the directions of the transition moments of the fluorescent molecules 14 are parallel. However, the shapes of fluorescent molecules and the transition moments are not necessarily parallel.

As described above, the relationship between the transition moments of the fluorescent molecules 14 and the vibration direction of the excitation light 19 influences the excitation efficiency of the fluorescent molecules 14. This fact also applies to the relationship between the transition moments of the fluorescent molecules 14 which are bound to the free molecules 20 and the binding molecules 22 and the vibration direction of the excitation light 19. Excitation efficiencies in the case that the free molecules 20 and the binding molecules 22 are excited by linearly polarized excitation light (polarization in which the vibration direction of light is in a single plane) will be described with reference to FIGS. 4A and 4B.

Figure 4B:
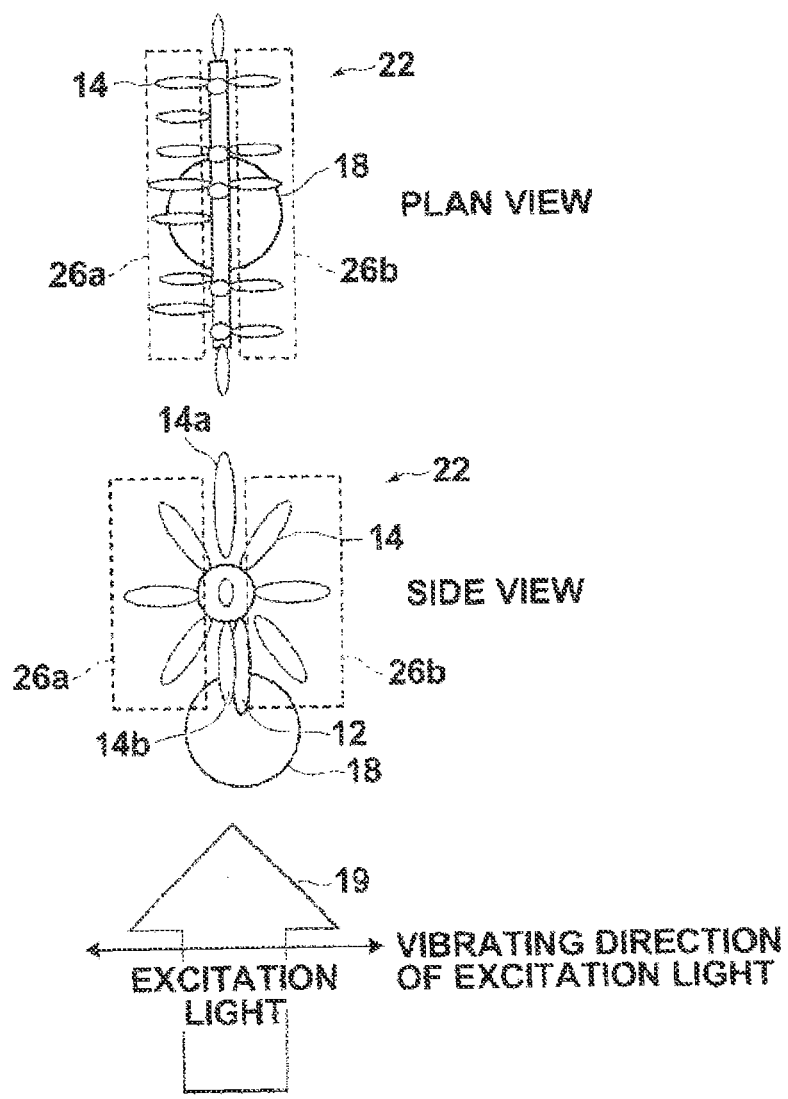
FIG. 4B is a diagram that illustrates a case in which the vibration direction of excitation light and the longitudinal direction of an orienting label are perpendicular.

As illustrated in FIGS. 4A and 4B, the fluorescent molecules 14 are bound to the lateral surfaces of the orientating labels 8 in a radial manner with respect to the central axes of the orienting labels 8. Accordingly, the directions of the transition moments of the fluorescent molecules 14, which are bound to the lateral surfaces of the orienting labels 8, are also radial with respect to the central axes of the orienting labels 8. In addition, the transition moments of the fluorescent molecules which are bound to the end surfaces of the orienting labels 8 of FIGS. 4A and 4B are parallel to the longitudinal directions of the orienting labels 8.

FIG. 4A is a diagram that illustrates a case in which the vibration direction of the excitation light 19 and the longitudinal direction of the orienting label 8 are parallel. In this case, the fluorescent molecules which are excited from among the plurality of fluorescent molecules 14 of the binding molecule 22 are mainly those which are bound to the two end surfaces of the orienting label (the fluorescent molecules within region 24a and region 24b indicated by the broken lines). The fluorescent molecules which are bound to the lateral surface of the orienting label 8 are not excited, because the transition moments thereof are perpendicular to the vibration direction of the excitation light.

FIG. 4B is a diagram that illustrates a case in which the vibration direction of the excitation light 19 and the longitudinal direction of the orienting label 8 are perpendicular. In this case, the fluorescent molecules which are excited from among the plurality of fluorescent molecules 14 of the binding molecule 22 are mainly those which are bound to the lateral surface of the orienting label 8 in a radial manner of which the transition moments are not perpendicular with the vibration direction of the excitation light 19 (the fluorescent molecules within region 26a and region 26b indicated by the broken lines). The fluorescent molecules which are bound to the two end surfaces of the orienting label 8 are not excited, because the transition moments thereof are perpendicular to the vibration direction of the excitation light. In addition, the fluorescent molecules, of which the transition moments are perpendicular to the vibration direction of the excitation light 19 (fluorescent molecule 14a and fluorescent molecule 14b, for example), from among the fluorescent molecules which are bound to the lateral surface of the orienting label 8 in a radial manner, are also not excited.

The orienting label 8 is of an elongate cylindrical shape. The area of the lateral surface of the orienting label 8 is greater than the area of the two end surfaces thereof. Therefore, a greater number of fluorescent molecules are bound to the lateral surface of the orienting label 8 compared to the two end surfaces thereof. Accordingly, a greater number of fluorescent molecules can be excited in the case that the vibration direction of the excitation light 19 and the longitudinal direction of the orienting label 8 are perpendicular compared to a case in which the vibration direction of the excitation light 19 and the longitudinal direction of the orienting label 8 are in a parallel positional relationship. That is, the total amount of fluorescence emitted from the binding molecule 22 changes, by changing the orientation direction of the orienting label 8 (the longitudinal direction of the orienting label 8) while maintaining the vibration direction of the excitation light 19 constant.

Note that strictly speaking, even in the case that the vibration direction of the excitation light 19 and the longitudinal direction of the orienting label 8 are parallel, if the fluorescent molecules 14 which are bound got the lateral surface of the orienting label 8 are bound in an oblique direction, the transition moments thereof will not be completely perpendicular with the vibration direction of the excitation light 19, and the fluorescent molecules 14 which are bound to the lateral surface of the orienting label 8 may be excited. However, the number of fluorescent molecules which are bound to the lateral surface of the orienting label 8 and of which the transition moments will not be perpendicular to the vibration direction of the excitation light 19 is very small compared to the total number of fluorescent molecules. Accordingly, if the binding molecules 22 are considered as a whole, the binding molecule 22 of such a rare case will not emit as much fluorescence as those in a case in which the vibration direction of the excitation light 19 and the longitudinal direction of the orienting label 8 are perpendicular. Similarly, there are cases in which some of the fluorescent molecules which are bound to the two end surfaces of the orienting label 8 are excited even in the case that the vibration direction of the excitation light 19 and the longitudinal direction of the orienting label 8 are perpendicular. However, the percentage of such fluorescent labels with respect to the binding molecules 22 as a whole is negligible.

Note that a description was given regarding the binding molecules 22 illustrated in FIGS. 4A and 4B. Fluorescent molecules of the free molecules 20 which are at the same positions as those of the binding molecules 22 are excited according to the relationship between the vibration direction of the excitation light 19 and the longitudinal direction of the orienting label 8 as well.

Motion of the free molecules 20 and the binding molecules 22 within the solution will be described in order to consider the orientations of the fluorescent molecules 14 within the solution. The free molecules 20 and the binding molecules 22 move irregularly (Brownian motion) within the solution, and undergo movement within the solution and rotational movement. It is known that Brownian motion of molecules within solutions is influenced by absolute temperature, the volumes of the molecules, the viscosity of the solution, etc. The volumes of the binding molecules 22 are greater than those of the free molecules 20 due to the antigens 18 being bound thereto, and are less likely to undergo Brownian motion within the solution. A technique that utilizes the difference in Brownian motion of free molecules 20 and binding molecules 22 within solutions to detect binding molecules 22 from changes in Brownian motion is known. However, because this technique utilizes Brownian motion, which is random, detection sensitivity is limited.

The biological molecule detecting apparatus according to the first embodiment of the present invention utilizes laser beams to control the orientations of molecules within the solution. When a laser beam is emitted onto the free molecules and the binding molecules within the solution, the orienting labels 8 receive external force, and the free molecules and the binding molecules which had been moving randomly within the solution become oriented in a specific direction (hereinafter, a state in which the molecules are oriented in a specific direction by receiving external force will be referred to as "complete molecular orientation"). The ease with which the free molecules and the binding molecules move and rotate within the solution differ due to differences in volume or mass. Therefore, in the case that the orientations of the molecules within the solution are controlled by the laser beam, the amount of time required for the free molecules and the binding molecules to complete molecular orientation from the time that the laser beam is emitted differ. The biological molecule detecting apparatus according to the first embodiment of the present invention utilizes the difference in the amounts of time required for the free molecules and the binding molecules to complete molecular orientation to generate differences in the excitation efficiencies of the fluorescent molecules 14 associated with each type of molecule and to calculate the fluorescence contributed by the binding molecules.

Figure 5A:
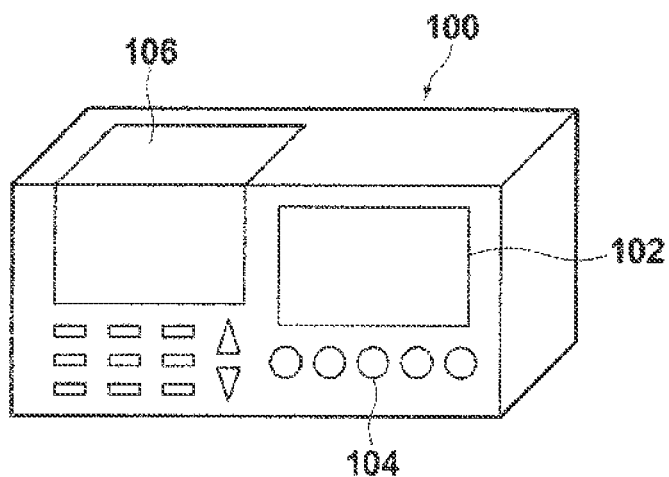
FIG. 5A is a perspective view that illustrates the outer appearance of the biological molecule detecting apparatus according to the first embodiment.

Next, the configuration of the biological molecule detecting apparatus 100 according to the first embodiment of the present invention will be described. FIG. 5A is a perspective view that illustrates the outer appearance of the biological molecule detecting apparatus 100. A display section 102, and a user input section 104, and an openable portion 106 are provided on a side surface of the biological molecule detecting apparatus 100. The display section 102 displays measurement results and the like. The user input section 104 is a section at which modes are set, sample data are input, etc. The openable portion 106 is of a configuration in which an upper lid may be opened. The upper lid is opened when samples are set, and closed during measurements. By adopting this configuration, light from the exterior influencing measurements can be prevented.

Figure 5B:
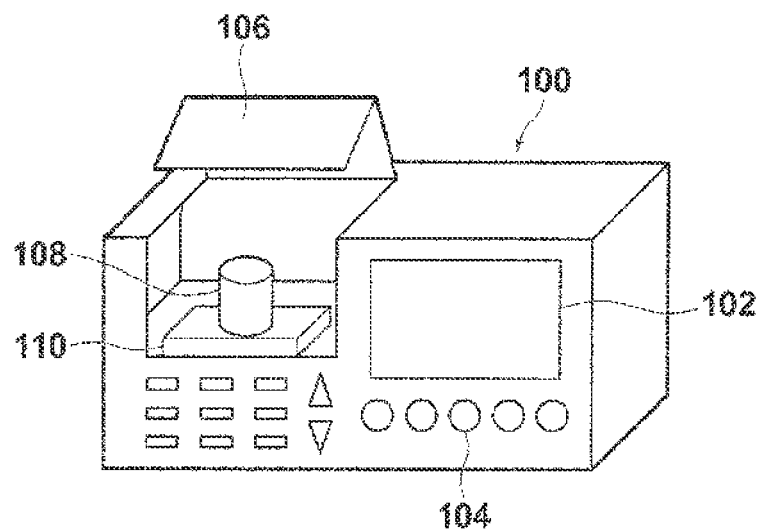
FIG. 5B is a diagram that illustrates the biological molecule detecting apparatus according to the first embodiment in a state in which an openable portion is opened.

FIG. 5B is a perspective view that illustrates the biological molecule detecting apparatus 100 in a state in which the openable portion 106 is opened. When the openable portion 106 is opened, a reagent cup 108 and a holding base 110 are present within the biological molecule detecting apparatus 100. The reagent cup 108 is removably held by the holding base 110. The reagent cup 108 is a cylindrical container in which solutions are placed. Users dispense samples into the reagent cup 108 and close the upper lid to perform measurements. Although not illustrated in the drawings, the biological molecule detecting apparatus 100 is also equipped with a reagent tank and a dispensing section. When measurements are initiated, the dispensing section suctions a reagent from within the reagent tank, and dispenses the reagent into the reagent cup 108.

Figure 6:
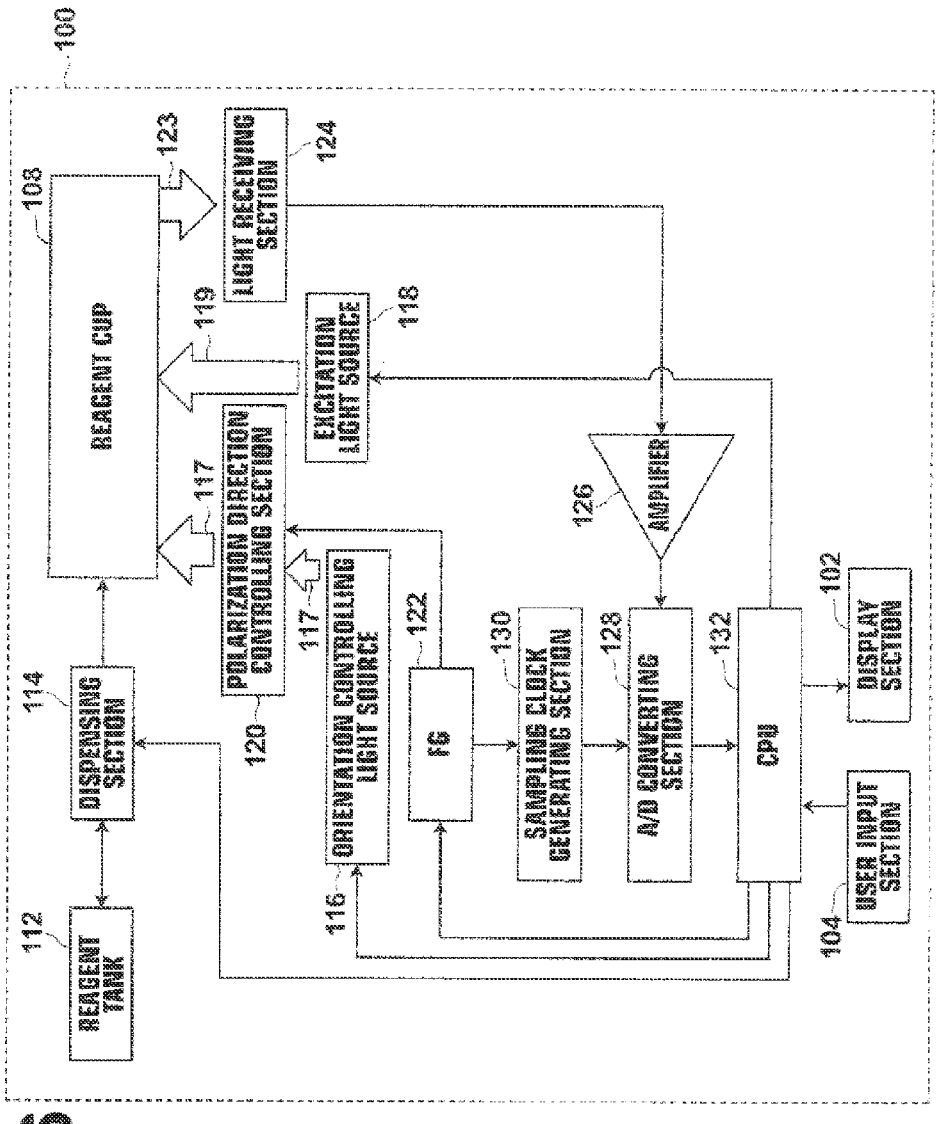
FIG. 6 is a block diagram that illustrates the main components of the biological molecule detecting apparatus.

FIG. 6 is a functional block diagram that illustrates the main components of the biological molecule detecting apparatus 100. The biological molecule detecting apparatus 100 includes: the display section 102, the user input section 104, the reagent cup 108, the reagent tank 112, the dispensing section 114, an orientation controlling light source 116, an excitation light source 118, an polarization direction controlling section 120, a FG (Function Generator) 122, a light receiving section 124, an amplifier 126, an A/D converting section 128, a sampling clock generating section 130, and a CPU 132.

The reagent cup 108 is a container in which reagents stored in the reagent tank 112 and samples collected from patients or the like are caused to react. The reagent cup 108 is removably attached to the biological molecule detecting apparatus 100. The capacity of the reagent cup 108 is approximately 120 μL.

The reagent tank 112 is a tank in which a plurality of types of reagents are stored. The free molecules 20 are stored in the reagent tank 112 as reagents.

The dispensing section 114 is constituted by a removably pipette, a suctioning device, etc. The dispensing section 114 suctions reagents to be utilized for measurement from the reagent tank 112 and dispenses the suctioned reagents to the reagent cup 108, according to commands from the CPU 132.

The orientation controlling light source 116 emits an orientation controlling light beam 117 which is linearly polarized by a polarizing element toward the polarization direction controlling section 120, and orients the free molecules 20 and the binding molecules 22 which are present in the solution within the reagent cup 108, by applying external force thereto. A laser beam having a wavelength of 1.3 μm and an output of 700 mW, for example, is employed as the orientation controlling light beam 117. The orientation controlling light beam 117 has a width capable of illuminating the entirety of the solution within the reagent cup 108.

The excitation light source 118 is provided under the reagent cup 108, and emits excitation light 119, which is linearly polarized by a polarizing element provided within the excitation light source 118, from the bottom toward the top of the reagent cup 108, to excite the fluorescent molecules 14. Light having a wavelength of 532 nm and an output of 10 mW, for example, is employed as the excitation light.

The polarization direction controlling section 120 switches the polarization direction (vibration direction) of the orientation controlling light beam 117, to switch the orientation directions of the free molecules 20 and the binding molecules 22. Note that the "orientation direction" of the free molecules and the binding molecules refers to the longitudinal directions of the orienting labels 8 after orientation is complete. The polarization direction controlling section 120 has a λ/2 wavelength plate. λ/2 wavelength plates are phase plates that function to cause optical path differences between two perpendicular components of light to change for half the wavelength thereof, and are employed to rotate the polarization planes of light. Light which is linearly polarized in a direction parallel to the direction of the optical axis of a λ/2 wavelength plate passes therethrough as is, whereas light which is linearly polarized in a direction that forms a 45 degree angle with the direction of the optical axis of a λ/2 wavelength plate is transmitted in a state in which the polarization axis thereof is rotated 90 degrees. That is, switching between a case in which light passes through the λ/2 wavelength plate as is and a case in which the light is transmitted in a state in which the polarization axis thereof is rotated 90 degrees is enabled, by switching the angle of the λ/2 wavelength plate with respect to the linearly polarized light. The polarization direction controlling section 120 rotates the λ/2 wavelength plate according to signals received from the FG 122, to switch the vibration direction of the orientation controlling light beam 117 by 90 degrees. In other words, the vibration direction of the orientation controlling light beam 117 is determined by voltage signals generated by the FG 122.

The FG 122 is a device capable of generating voltage signals having various frequencies and waveforms. The FG 122 outputs different voltage signals to the polarization direction controlling section 120 and the sampling clock generating section 130 in response to commands received from the CPU 132. Hereinafter, the voltage signals output to the polarization direction controlling section 120 from the FG 122 will be referred to as orientation control signals.

The CPU 132 controls the operations of the biological molecule detecting apparatus 100 as a whole, performs calculations of measurement results, etc. The CPU 132 specifies orientation control signals to be output by the FG 122, and controls the timings at which the polarization direction controlling section 120 switches the vibration direction of the orientation controlling light bean 117.

The light receiving section 124 is provided under the reagent cup 108. The light receiving section 124 receives fluorescence 123 generated by the fluorescent molecules 14 within the reagent cup 108 under the reagent cup 108, converts the received fluorescence signals to analog electrical signals (analog fluorescence data), and outputs the analog electrical signals to the amplifier 126.

The amplifier 126 amplifies the analog fluorescence data output thereto from the light receiving section 124, and outputs the amplified analog fluorescence data to the A/D converting section 128.

The sampling clock generating section 130 inputs a sampling clock that specifies the timings at which the A/D converting section 128 is to sample the analog fluorescence data to the A/D converting section 128, based on voltage signals output thereto from the FG 122.

The A/D converting section 128 samples the analog fluorescence data output thereto from the amplifier 126, based on the sampling clock output thereto from the sampling clock generating section 130. The A/D converting section 128 converts the sampled analog fluorescence data to digital data, and outputs the digital data to the CPU 132.

The CPU 132 performs calculations using the digital data output thereto from the A/D converting section 128, and outputs the results of calculations to the display section 102. In addition, the CPU 132 controls the operations of the orientation controlling light source 116, the excitation light source 118, the dispensing section 114, and the FG 122 in response to commands input from the user input section 104. Specifically, the CPU 132 outputs ON/OFF commands to the orientation controlling light source 116 and the excitation light source 118, outputs commands that specify a reagent to be utilized and commands to initiate dispensing operations to the dispensing section 114, and outputs commands that specify the waveform of voltage signals to be output and commands to output the voltage signals to the FG 122.

Movement of the free molecules 20 and the binding molecules accompanying switches in the vibration direction of the orientation controlling light beam 117 emitted by the orientation controlling light source 116 will be described with reference to the schematic diagrams of FIGS. 7A through 7C.

The orientation controlling light beam 117 emitted from the orientation controlling light source 116 passes through the polarization direction controlling section 120 and enters the reagent cup 108. The polarization direction controlling section 120 alternately switches the vibration direction of the orientation controlling light beam 117 emitted from the orientation controlling light source 116 between two directions. Specifically, the polarization direction controlling section 120 causes the orientation controlling light beam 117 to pass therethrough as is in the case that a 0V orientation control signal is input thereto from the FG 122, and switches the vibration direction of the orientation controlling light beam 117 by 90 degrees in the case that a 5V orientation control signal is input thereto from the FG 122. In the present embodiment, the vibration direction of the orientation controlling light beam 117 that enters the reagent cup 108 is parallel to the vibration direction of the excitation light beam 119 in the case that the orientation controlling light beam 117 passes through the polarization direction controlling section 120 as is. Accordingly, the vibration direction of the orientation controlling light beam 117 that enters the reagent cup 108 is perpendicular to the vibration direction of the excitation light beam 119 in the case that the polarization direction controlling section 120 switches the vibration direction of the orientation controlling light beam 117 by 90 degrees.

The orientation controlling light beam 117 orients the free molecules 20 and the binding molecules 22 by imparting external force thereon. The external force exerted by the orientation controlling light beam 117 is generated by reactions to the orientation controlling light beam 117 hitting the free molecules 20 and the binding molecules 22 and being scattered. Accordingly, the direction in which the force is exerted by the orientation controlling light beam 117 is determined by the direction in which the orientation controlling light beam 117 vibrates and the orientations of the free molecules and binding molecules. The free molecules 20 and the binding molecules 22 are dispersed within the solution oriented in random directions. However, the free molecules 20 and the binding molecules 22 receive force that cause them to rotate a small amount (rotational direction) by the orientation controlling light beam 117 when the orientation controlling light beam 117 is irradiated thereon. The free molecules 20 and the binding molecules 22 that receive the effect of the orientation controlling light beam 117 stabilize in an orientation in a direction in which the external forces in various rotational directions imparted by the orientation controlling light beam 117 balance out. In this case, that the free molecules 20 and the binding molecules are oriented in a direction in which the forces in the rotational directions imparted by the orientation controlling light beam 117 means that the longitudinal directions of the orienting labels become parallel to the vibration direction of the orientation controlling light beam 117. Accordingly, the directions in which the free molecules 20 and the binding molecules 22 are oriented can be changed by changing the vibration direction of the orientation controlling light beam 117.

FIG. 7A is a collection of diagrams that show the orientation directions of the free molecules 20 and the binding molecules 22 in the case that the polarization direction controlling section 120 causes the orientation controlling light beam 117 to pass therethrough as is. When the orientation controlling light beam 117 that vibrates in the horizontal direction of the drawing sheet enters the reagent cup 108, the free molecules 20 and the binding molecules 22 become oriented such that the longitudinal directions of the orienting labels 8 are parallel with the vibration direction of the orientation controlling light beam 117.

Figure 7B:
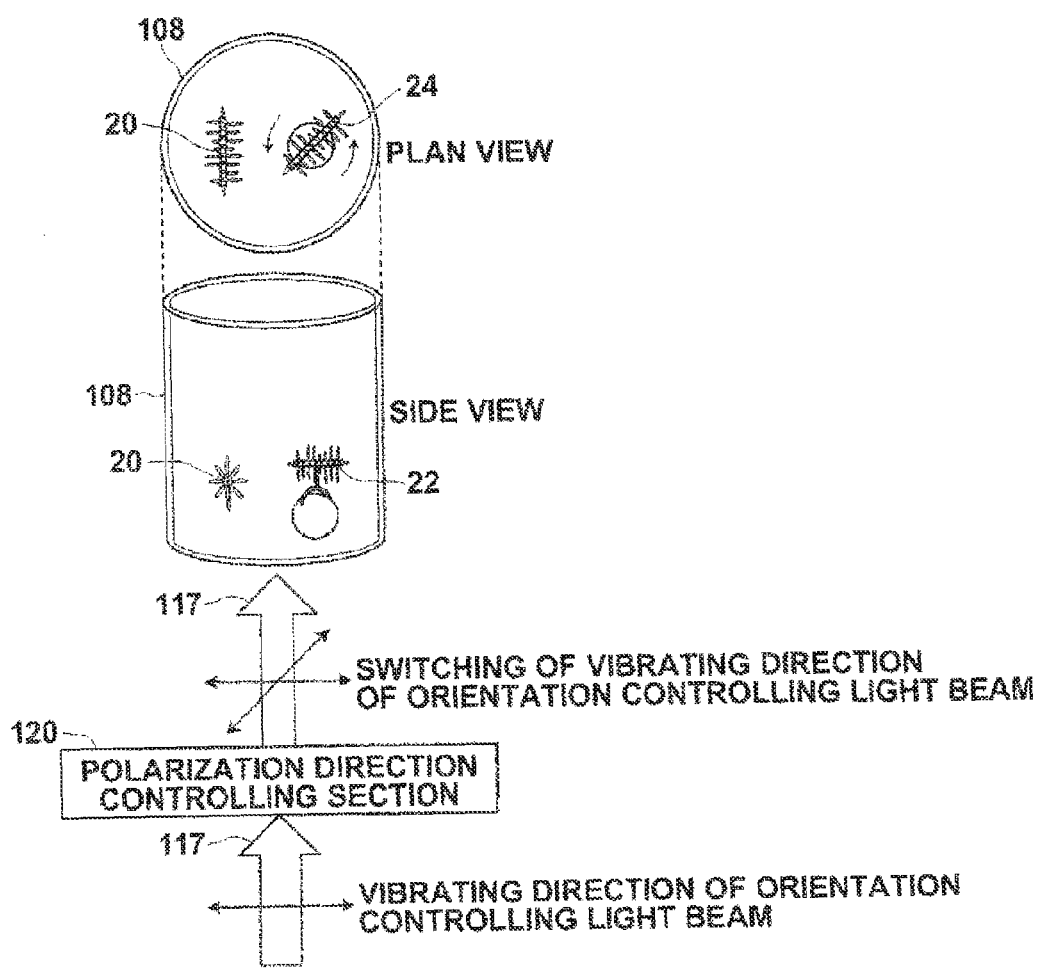
FIG. 7B is a collection of diagrams that illustrates the motion of a free molecule and a binding control when the vibration direction of an orientation controlling light beam is switched.

FIG. 7B is a collection of diagrams that show the movement of the free molecules 20 and the binding molecules 22 when the vibration direction of the orientation controlling light beam 117 is switched 90 degrees such that the orientation controlling light beam 117 vibrates in a direction perpendicular to the plane of the drawing sheet. When a 5V orientation controlling signal is output from the FG 122, the polarization direction controlling section 120 switches the vibration direction of the orientation controlling light beam 117 to the direction perpendicular to the plane of the drawing sheet. When the orientation controlling light beam 117 that vibrates in the horizontal direction of the drawing sheet enters the reagent cup 108, the free molecules 20 and the binding molecules 22 rotate such that such that the longitudinal directions of the orienting labels 8 are parallel with the vibration direction of the orientation controlling light beam 117. In this case, the free molecules 20 which have smaller volumes and masses than the binding molecules 22 rotate faster, and the time required for reorientation thereof to become complete is shorter. The reorientation of the binding molecules 22 is completed at a later time than that when the reorientation of the free molecules 20 becomes complete.

FIG. 7C is a collection of diagrams that illustrates the orientation directions of the free molecules 20 and the binding molecules 22 of which orientation has been completed in a case that the orientation controlling light beam 117 is vibrating in the direction perpendicular to the plane of the drawing sheet. In the case that the vibration direction of the orientation controlling light beam 117 is direction perpendicular to the plane of the drawing sheet, the free molecules 20 and the binding molecules 22 become oriented such that the longitudinal directions of the orienting labels 8 are perpendicular to the plane of the drawing sheet.

The biological molecules detecting apparatus 100 is capable of switching the vibration direction of the orientation controlling light beam 117 and the orientation directions of the free molecules 20 and the binding molecules 22 in two directions having an angular difference of 90 degrees, by switching the orientation of the λ/2 wavelength sheet of the polarization direction controlling section 120 according to the orientation controlling signals input by the FG 122.

The relationship between the orientation directions of the free molecules 20 and the binding molecules 22 and the excitation light 119 will be described with reference to FIGS. 8A and 8B.

FIG. 8A is a schematic diagram that illustrates the relationship between an oriented free molecule 20 and an oriented binding molecule 22 and the vibration direction of the excitation light 119 in the case that the orientation control signal output from the FG 122 to the polarization direction controlling section 120 is 0V.

In the case that the orientation control signal output from the FG 122 to the polarization direction controlling section 120 is 0V, the vibration direction of the excitation light 119 and the longitudinal directions of the orienting labels 8 will be parallel. In this case, mainly the fluorescent molecules 14 are bound to the two end surfaces of the orienting label 8 are excited, from among the plurality of fluorescent molecules 14 of the free molecules 20 and the binding molecules 22. This is because the transition moments of the fluorescent molecules bound to the two end surfaces of the orienting labels 8 are not perpendicular to the vibration direction of the excitation light 119. The fluorescent molecules 14 which are bound to the lateral surfaces of the orienting labels 8 are not excited, because the transition moments thereof are perpendicular to the vibration direction of the excitation light 119.

FIG. 8B is a schematic diagram that illustrates the relationship between an oriented free molecule 20 and an oriented binding molecule 22 and the vibration direction of the excitation light 119 in the case that the orientation control signal output from the FG 122 to the polarization direction controlling section 120 is 5V.

In the case that the orientation control signal output from the FG 122 to the polarization direction controlling section 120 is 5V, the vibration direction of the excitation light 119 and the longitudinal directions of the orienting labels 8 will be perpendicular to each other. In this case, mainly the fluorescent molecules 14 are bound to the lateral surfaces of the orienting label 8 are excited, from among the plurality of fluorescent molecules 14 of the free molecules 20 and the binding molecules 22. This is because the transition moments of the fluorescent molecules bound to the lateral surfaces of the orienting labels 8 are not perpendicular to the vibration direction of the excitation light 119. The fluorescent molecules 14, which are bound to the two end surfaces of the orienting labels 8, and a portion of the fluorescent molecules 14, which are bound to the lateral surfaces of the orienting labels 8 and of which the transition moments are perpendicular to the vibration direction of the excitation light 119, are not excited because the transition moments thereof are perpendicular to the vibration direction of the excitation light 119.

The amount of light emitted by each free molecule 20 or each binding molecule 22 is greater in the case that the orientation control signal output to the polarization direction controlling section 120 from the FG 122 is 5V than a case that the orientation control signal is 0V because a greater number of fluorescent molecules 14 are bound to the lateral surfaces of the orienting labels 8 than to the two end surfaces thereof. For this reason, the total amount of fluorescence emitted from within the solution in the reagent cup 108 is greater in the case that the orientation control signal output to the polarization direction controlling section 120 from the FG 122 is 5V.

The switching of the vibration direction of the orientation controlling light beam 117 by the polarization direction controlling section 120 switches the amount of light emitted by each free molecules 20 and each binding molecule 22 in this manner. Meanwhile, because the volumes and masses of the free molecules 20 and the binding molecules 22 are different, the speeds at which the orientations thereof are switched in response to the switch of the vibration direction of the orientation controlling light beam 117 also differ.

The free molecules 20 have smaller volumes and masses compared to the binding molecules 22. Therefore, the orientations of the free molecules 20 change faster in response to switches in the vibration direction of the orientation controlling light beam 117 than the orientations of the binding molecules 22. That is, the timing at which the amount of light emitted by each molecule increases is quicker for the free molecules 20 than the binding molecules 22, because reorientation thereof is completed faster. The biological molecule detecting apparatus 100 utilizes the fact that the timings at which the amounts of light emitted by the free molecules 20 and the binding molecules 22 switch accompanying the switch in the vibration direction of the orientation controlling light beam 117 are different, to separate the amount of fluorescence contributed by the free molecules 20 and the amount of fluorescence contributed by the binding molecules 22 with respect to the total amount of emitted light.

Next, the detailed structure of the light receiving section 124 will be described with reference to FIG. 9. FIG. 9 is a schematic diagram that illustrates the detailed structure of the light receiving section 124. The light receiving section 124 includes: a lens 142; a filter 144; a polarizing element 146; a lens 148; and a PD (photodiode) 150.

The light receiving section 124 receives fluorescence from the bottom side of the reagent cup 108. Fluorescence 147 emitted by the free molecules 20 or the binding molecules 22 within the reagent cup 108 and enters the light receiving section 124 toward the left side of the drawing sheet, and fluorescence 149 emitted by the free molecules 20 or the binding molecules 22 and enters the light receiving section 124 toward the right side of the drawing sheet are focused and collimated by the lens 142, then enter the polarizing element 146 after passing through the filter 144. Note that although not illustrated in FIG. 9, fluorescence is present between the fluorescence 147 and the fluorescence 149. However, the behavior of such fluorescence is predictable by those skilled in the art, and therefore a description thereof will be omitted.

The filter 144 is a band pass filter that cuts off light other than the fluorescence emitted by the fluorescent molecules 14, and prevents light other than the fluorescence, such as the excitation light, from entering the PD 150.

The polarizing element 146 only transmits light which is polarized in the same direction as the vibration direction of the linearly polarized excitation light 119. That is, if the fluorescent molecules 14 which are not undergoing movements such as Brownian motion are excited by the linearly polarized excitation light 119, the fluorescence emitted by these fluorescent molecules 14 is also light which is linearly polarized in the same direction as the vibration direction of the excitation light. For this reason, fluorescence emitted by the free molecules 20 or the binding molecules 22, of which orientation has been completed, can pass through the polarizing element 146. The excitation light 119 which is scattered within the reagent cup 108 and fluorescence emitted by the fluorescent molecules 14 while the directions of the orientations of the free molecules 20 and the binding molecules 22 are being switched have vibration directions different from the original vibration direction of the excitation light 119, and therefore cannot be transmitted through the polarizing element 146. The polarizing element 146 transmits only fluorescence emitted by fluorescent molecules 14 associated with the free molecules 20 and the binding molecules 22, of which orientation has been completed, in this manner.

The PD 150 receives the fluorescence focused by the lens 148, generates electric charges corresponding to the intensity of the fluorescence focused by the lens 148, and outputs the electrical charges to the amplifier 126. In this manner, the light receiving section 124 converts the fluorescence emitted by the fluorescent molecules 14, of which orientation has been completed, into electrical charges.

Figure 10:
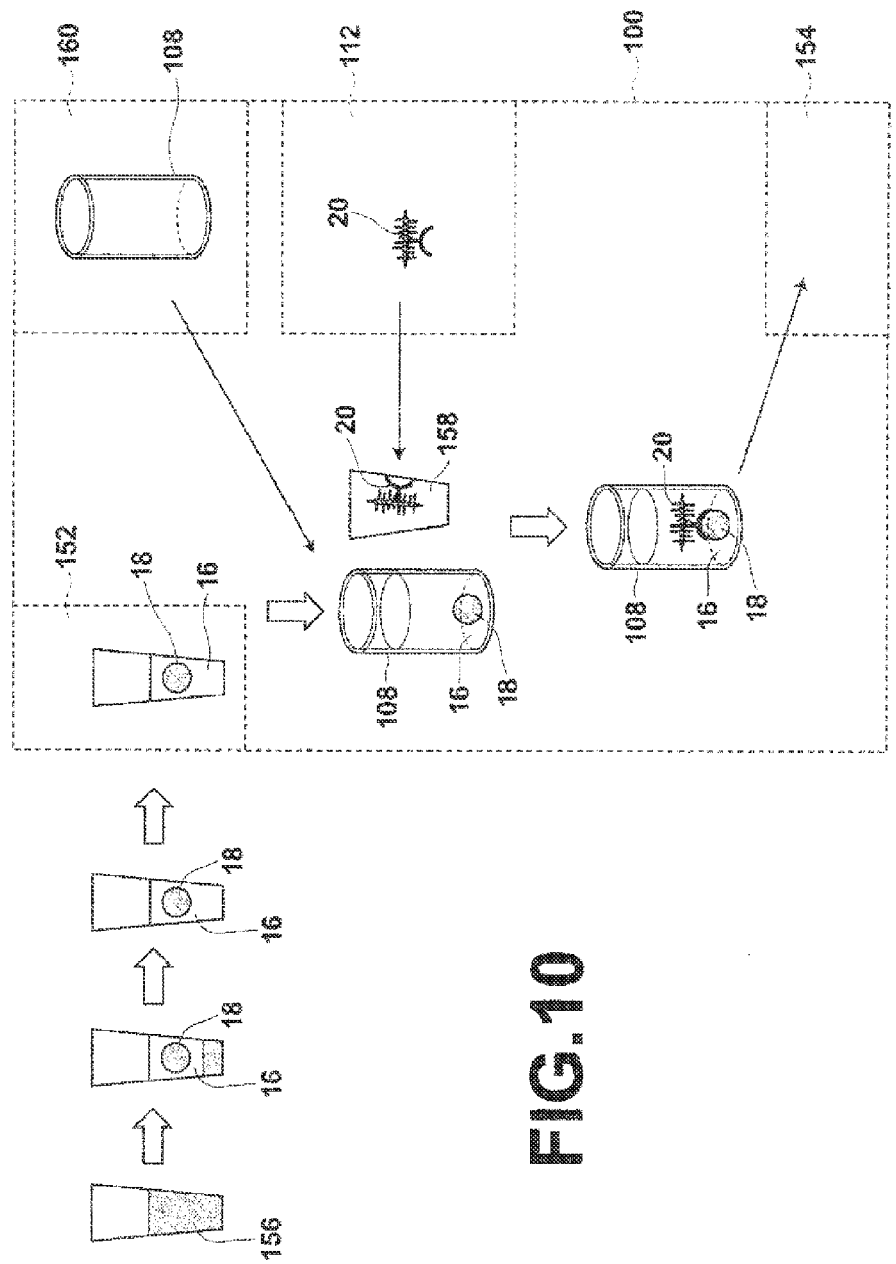
FIG. 10 is a diagram that schematically illustrates the flow of a process from preparation of a sample through disposal thereof.

Next, the operations of the biological molecule detecting apparatus 100 during measurements will be described. FIG. 10 is a diagram that schematically illustrates the flow of a process from preparation of a sample through disposal thereof.

To prepare for measurement, first, 50 μL of whole blood 156 collected from a patient is centrifugally separated to separate plasma 16. The separated plasma 16 is set in a sample setting section 152 of the biological molecule detecting apparatus 100. The steps up to this point are performed by a user.

The biological molecule detecting apparatus 100 dispenses the plasma 16, which is set in a sample setting section 152, into a new reagent cup 108, which is stocked in a reagent cup stocking section 160. Next, the biological molecule detecting apparatus 100 suctions the free molecules 20, which are in the reagent tank 112, with a pipette 158, and dispenses the suctioned free molecules 20 into the reagent cup 108. After the plasma 16 and the free molecules 20 are injected into the reagent cup 108, the biological molecule detecting apparatus 100 uses a built in vortex mixer to agitate the reagent cup 108 while maintaining the temperature of the reagent cup 108 at 37° C. to cause antigen antibody reactions to occur. Thereafter, the biological molecule detecting apparatus 100 emits excitation light, detects fluorescence, and disposes of the reagent cup 108 into a built in trash receptacle 154 after the fluorescence is detected.

The orientation control signals output by the FG 122, the sampling clock output by the sampling clock generating section 130, the PD outputs output by the PD 150, and the A/D conversion outputs output by the A/D converting section 128 will be described with reference to FIG. 11. FIG. 11 is a collection of graphs having voltages of orientation control signals, voltages of sampling clocks, PD outputs, and A/D converting section outputs as vertical axes, respectively, and time t as the horizontal axes. Note that here, the graphs of the PD outputs and the A/D converting section outputs are illustrated schematically in order to simplify the description.

The orientation control signal output by the FG 122 is 0V prior to measurement. The orientation controlling light beam 117 is emitted into the solution to orient the free molecules 20 and the binding molecule 22 prior to measurement. In the case that the orientation control signal is 0V, the sampling clock is also 0V, and sampling is not performed. The A/D converting section output is also 0 because the sampling clock is not input. When the excitation light is emitted toward the reagent cup 108 while the orientation control signal is 0V, the PD output becomes an initial value iz, which is a sum of the output due to the fluorescent molecules 14 which are bound to the two end surfaces of the orienting labels 8 of the free molecules 20 and the binding molecules 22, and noise due to the apparatus itself.

Next, the biological molecule detecting apparatus 100 changes the orientation control signal to 5V. When the orientation control signal is changed to 5V, the sampling clock generating section 130 periodically outputs a 5V signal as a sampling clock that represents sampling timings. The A/D converting section 128 samples analog fluorescence data at timings that match the sampling clock and performs A/D conversion.

In addition, when the orientation control signal is changed to 5V, the polarization direction controlling section 120 switches the vibration direction of the orientation controlling light beam 117 by 90 degrees. Accompanying the switch in the vibration direction of the orientation controlling light beam 117, the directions in which the free molecules 20 and the binding molecules 22 within the reagent cup 108 are oriented are also switched by 90 degrees.

In this case, the directions of orientations of the free molecules 20, which have smaller volumes than the binding molecules 22, switch faster. A majority of the fluorescence emitted by the fluorescent molecules 14 associated with the free molecules 20 and the binding molecules 22 during the switch in orientations thereof is not polarized, and therefore is cut off by the polarizing element 146.

The free molecules 20 for which orientation has been completed emit a greater amount of fluorescence compared to the amount of fluorescence emitted prior to the switch in orientation becoming complete. The fluorescence emitted by the fluorescent molecules associated with the free molecules 20, of which orientation has been completed, reach the PD 150 without being cut off by the polarizing element 146, because it is polarized in the same direction as the vibration direction of the excitation light. Accompanying the increase in the number of free molecules 20 for which orientation has been completed, the PD output increases from iz. When orientation of all of the free molecules 20 is completed at time T1, the PD output is temporarily saturated at value if.

Thereafter, when orientation of the binding molecules 22 begins at time T2, the PD output increases again. A majority of the fluorescence emitted by the fluorescent molecules 14 associated with the binding molecules during the switch in orientations thereof is not polarized, and therefore is cut off by the polarizing element 146. When orientation of all of the binding molecules is completed at time T3, the PD output is saturated at value i.

The output of the A/D converting section is initially a value Dz, similar to the PD output, then gradually increases and becomes temporarily saturated at a value Df. The output of the A/D converting section gradually increases accompanying the increase in the PD output from if, and becomes saturated at a value Dt. By setting the orientation control signal to be 0V and then changing it to 5V in this manner, the fluorescence contributed by the fluorescent molecules associated with the free molecules 20 and the fluorescence contributed by the fluorescent molecules associated with the binding molecules 22 will appear in the output of the A/D converting section with a temporal difference therebetween.

The orientation control signal is changed back to 0V after being output as 5V for T seconds. T seconds is set to be greater than or equal to the amount of time required for the output of the PD to become saturated a second time at the value it. By the orientation control signal being switched back to 0V from 5V, the sampling clock will also become 0V. After the orientation control signal is switched from 5V to 0V, the PD output will be the value it for an amount of time, and then decrease to the value iz. The reason why the PD output becomes the value iz is because the longitudinal directions of the orienting labels 8 of the free molecules 20 and the binding molecules 22 become parallel to the vibration direction of the excitation light due to the orientation control signal being switched to 0V, and the amounts of fluorescence which are emitted by each of the free molecules 20 and the binding molecules 22 decrease. The reason why the PD output is the value it for an amount of time is because the switching of the orientation directions of the free molecules 20 and the binding molecules 22 is slightly delayed from the switching of the orientation control signal.

Here, the period of time during which the orientation control signal is set at 0V is T seconds, which is the same amount of time that the orientation control signal was set at 5V. This is because the amount of time required for the free molecules and the binding molecules within the solution to complete being reoriented is approximately the same for a case that the orientation control signal 117 is switched from 0V to 5V and a case that the orientation control signal is switched from 5V to 0V, under conditions that the output of the orientation controlling light beam 117 is constant. A single measurement cycle of the biological molecule detecting apparatus 100 is from the point in time that the orientation control signal is switched from 0V to 5V to a point in time T seconds after orientation control signal is switched back to 0V. That is, the amount of time in a single measurement cycle of the biological molecule detecting apparatus 100 is 2T seconds.

FIG. 12 is a graph that illustrates orientation control signals for a plurality of cycles in the biological molecule detecting apparatus 100. As illustrated in FIG. 12, the biological molecule detecting apparatus 100 performs a plurality of measurement cycles by switching the orientation control signals at predetermined temporal intervals, calculates arithmetic means for each of a plurality of values Dt, Df, and Dz, and obtains the average values for Dt, Df, and Dz. In the present embodiment, 10 measurement cycles are performed to obtain the average values for Dt, Df, and Dz. Thereby, fluctuations in measurement results caused by a variety of factors can be averaged out.

The CPU 132 calculates the concentration of the binding molecules from the obtained average values for Dt, Df, and Dz. Specifically, first, a measurement value S is calculated according to Formula (1) below.

$$S=(Dt-Df)/(Dt-Dz) \qquad (1)$$

In Formula (1), (Dt−Df) represents the increase in the intensity of fluorescence accompanying the switch in the orientation directions of the binding molecules 22. (Dt−Dz) represents the intensity of combined fluorescence emitted by the free molecules 20 and the binding molecules 22, and is calculated by subtracting the initial data from the maximum obtained data value. Factors that deteriorate the reproducibility of measurement results, such as changes in optical systems, are canceled by dividing (Dt−Df) by (Dt−Dz).

The CPU 132 calculates a diagnostic value C (the concentration of the detection target substance) from the obtained measurement value S. The diagnostic value C is calculated according to Formula (2) below.

$$C=f(S) \qquad (2)$$

Here, f(S) is a calibration curve function. The biological molecule detecting apparatus 100 has different calibration curve functions for each item to be measured prepared in advance, and converts the measurement value S to the diagnostic value C. The CPU 132 outputs the obtained diagnostic value C to the display section 102.

As described above, the biological molecule detecting apparatus 100 according to the first embodiment of the present invention is of a configuration that switches the vibration direction of the orientation controlling light beam 117, thereby enabling switching of the orientation directions of the free molecules 20 and the binding molecules 22 within the solution. The orientation states of the free molecules 20 and the binding molecules 22 which are oriented by the orientation controlling light beam 117 are that in which the longitudinal directions of the orienting labels 8 of the free molecules 20 and the binding molecules 22 are parallel to the vibration direction of the linearly polarized excitation light 119, and that in which the longitudinal directions of the orienting labels 8 of the free molecules 20 and the binding molecules 22 are perpendicular to the vibration direction of the linearly polarized excitation light 119. That is, the biological molecule detecting apparatus 100 switches the amounts of light emitted by each of the free molecules 20 and each of the binding molecules 22, by switching the vibration direction of the orientation controlling light beam 117. In addition, there is a difference in the amounts of time required for orientation of the free molecules 20 and orientation of the binding molecules 22 to become complete accompanying switching of the vibration direction of the orientation controlling light beam 117. Therefore, the timings at which the amounts of light emitted by each type of molecule increase differ. Accordingly, the biological molecule detecting apparatus 100 can calculate the fluorescence contributed by the fluorescent molecules associated with the free molecules and the fluorescence contributed by the fluorescent molecules associated with the binding molecules separately, and the concentration of the detection target substance can be accurately measured with a simple structure.

In the configuration described above, the biological molecule detecting apparatus 100 switches the orientations of all of the free molecules 20 and the binding molecules 22 into the same direction by the external force exerted by the orientation controlling light beam 117. Therefore, measurements having higher sensitivity can be performed compared to cases in which measurements are performed utilizing Brownian motion, which is random.

The free molecules 20 and the binding molecules 22 were provided with the orienting labels 8. Therefore, the orientations of the free molecules 20 and the binding molecules 22 can be switched by the orientation controlling light beam 117 even in cases that the molecular weight of the antibodies 12 is too low for the orientations thereof to be changed by the orientation controlling light beam 117. As a result, highly sensitive measurements are enabled. In addition, even in cases that the molecular weight of the antigens is sufficiently high, the S/N ratio can be improved by employing the orienting labels 8.

Note that the present embodiment was described as a case in which antigen antibody reactions are utilized as an example. However, the combination of the detection target substance and the substance that specifically binds with the detection target substance is not limited to the case described above. For example, the present invention may be applied to cases in which antigens are employed to detect antibodies, cases in which a specific nucleic acid is employed to detect a nucleic acid that hybridizes with the specific nucleic acid, cases in which nucleic acids are employed to detect nucleic acid binding proteins, cases in which ligands are employed to detect receptors, cases in which sugars are employed to detect lectin, cases in which protease detection is utilized, cases in which higher order structure changes are utilized, etc.

In the present embodiment, calculations were described for a case in which the graph illustrating measurement results is a schematic graph, to simplify the description of the calculation of the concentration of the detection target substance from the measurement results. However, it is not necessary for calculations to be performed in the manner described above. For example, a boundary point between fluorescence emitted by free molecules and fluorescence emitted by binding molecules may be determined based on the inflection point within a graph, to perform calculations.

In addition, it is desirable for the period of time during which the orientation control signal is set to 5V or 0V to be changed, based on the volumes of the free molecules and the binding molecules, the viscosity of the solution, the temperature of the solution, etc. The amount of time required for reorientation of the molecules to become complete following switching of the emission direction of the laser beam is determined by the ease with which the free molecules and the binding molecules rotate within the solution, which is influenced by the volumes of the free molecules and the binding molecules, the viscosity of the solution, the temperature of the solution, etc. In cases that it is difficult for the free molecules and the binding molecules to rotate within the solution, the amount of time required for orientation of the free molecules and the binding molecules to be completed will become longer. Therefore, it is desirable for the period of time during which the orientation control signal is set to 5V or 0V to be long enough for reorientation to be completed.

In addition, the present embodiment employed a laser beam having a wavelength of 1.3 μm and an output of 700 mW as the orientation controlling light beam 117. However, the orientation controlling light beam 117 is not limited to such a laser beam. It is desirable for the wavelength and the output of the laser light source to be determined based on the ease with which the free molecules and the binding molecules rotate within the solution, which is influenced by the volumes of the free molecules and the binding molecules, the masses of the free molecules and the binding molecules, etc. Particularly, it is desirable for a laser having an output to a degree that results in a difference to be exhibited in the amounts of time required for orientation of the free molecules and the binding molecules to become complete.

The present embodiment employed light having a wavelength of 532 nm and an output of 10 mW as the excitation light 119. However, the light to be employed as the excitation light 119 is not limited to such light.

Note that the present embodiment was described as a case in which measurements were repeatedly performed and arithmetic means of the measurement results were obtained. However, calculation of the arithmetic mean is not necessary, and the calculations may be determined according to what is important to a user. For example, in the case that a user wishes to perform measurements expediently, measurement may be performed for only a single cycle and the results of the measurement may be displayed. Alternatively, in the case that a user wishes to perform measurements with higher precision, measurements may be repeated for a plurality of cycles, to improve the measurement accuracy.

Second Embodiment

Figure 13A:
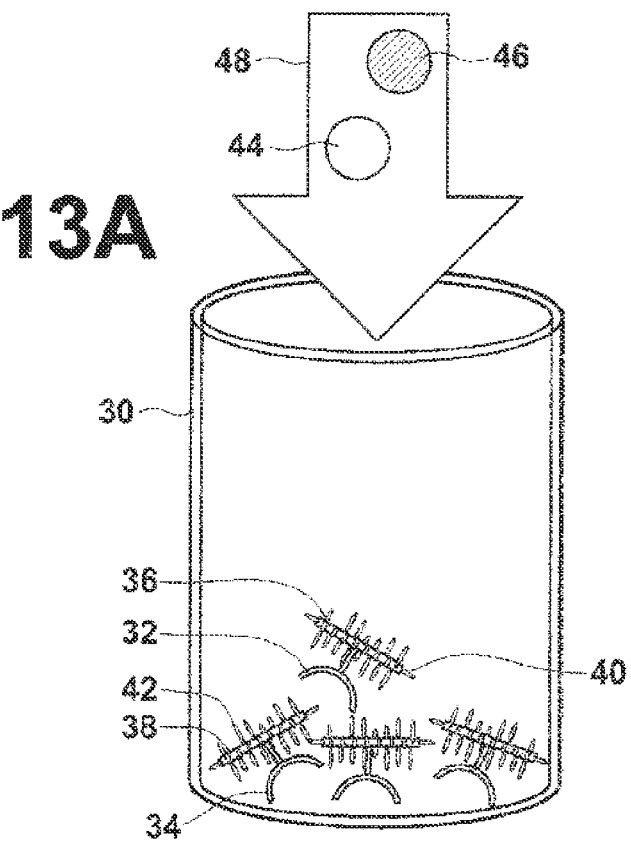
FIG. 13A is a first schematic diagram that illustrates antigen antibody reactions in a biological molecule detecting apparatus according to a second embodiment.
Figure 13B:
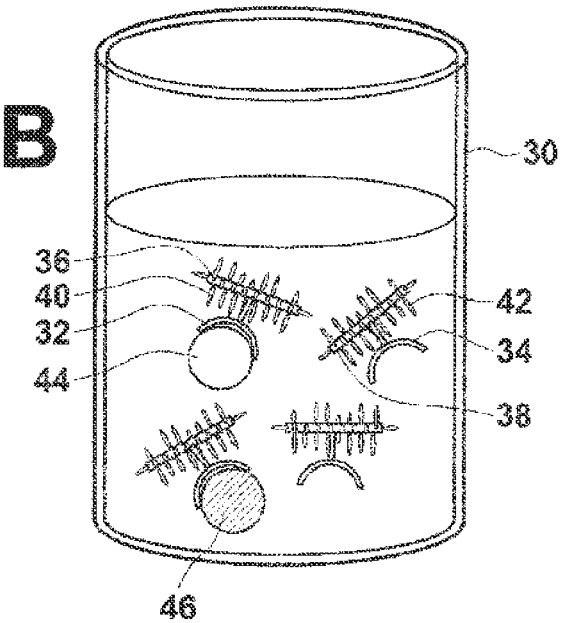
FIG. 13B is a second schematic diagram that illustrates antigen antibody reactions in the biological molecule detecting apparatus according to the second embodiment.

FIGS. 13A and 13B are schematic diagrams that illustrate antigen antibody reactions in a biological molecule detecting apparatus according to a second embodiment. The second embodiment utilizes two types of antibodies to detect two types of antigens within a single solution. Hereinafter, a case will be considered in which antibodies 32 and antibodies 34 are placed within a reagent cup 30. The antibodies 32 are bound to orienting labels 36 and fluorescent molecules 40 to form free molecules (hereinafter, referred to as free molecules A). The antibodies 34 are bound to orienting labels 38 and fluorescent molecules 42 to form free molecules (hereinafter, referred to as free molecules B).

When a sample 30 is placed in the reagent cup 48 and agitated, and if antigens 44 that specifically bind with the antibodies 32 are present in the sample 30, antigen antibody reactions will occur between the free molecules A and the antigens 44, causing the antibodies 32 and the antigens 44 to specifically bind with each other. Similarly, if antigens 46 that specifically bind with the antibodies 34 are present in the in the sample 30, antigen antibody reactions will occur between the free molecules B and the antigens 44, causing the antibodies 34 and the antigens 46 to specifically bind with each other. In the same manner as that described with respect to the first embodiment, a portion of the antibodies remain within the sample solution without undergoing antigen antibody reactions. Hereinafter, the free molecules A and the antigens 44 which are bound to each other by antigen antibody reactions will be referred to as binding molecules A, and the free molecules B and the antigens 46, which are bound to each other by antigen antibody reactions will be referred to as binding molecules B. In the present embodiment, the antigens 44 and the antigens 46, which are detection target substances, are PSA and SCC (Squamous Cell Carcinoma) antigens, respectively. Anti PSA antibodies that specifically bind to PSA are employed as the antibodies 32, and SCC antibodies that specifically bind to SCC antigens are employed as the antibodies 34. Alexa Fluor 568 by Molecular Probes is employed as the fluorescent molecules 40, and Alexa Fluor 555 by Molecular Probes is employed as the fluorescent molecules 42. Alexa Fluor 555 emits fluorescence having wavelengths within a range from 540 nm to 700 nm, and emits fluorescence having a wavelength of approximately 570 nm most intensely.

The biological molecule detecting apparatus according to the second embodiment of the present invention emits excitation light onto the solution, in which the two types of free molecules and the two types of binding molecules are present, and detects or quantifies target binding molecules.

Figure 14:
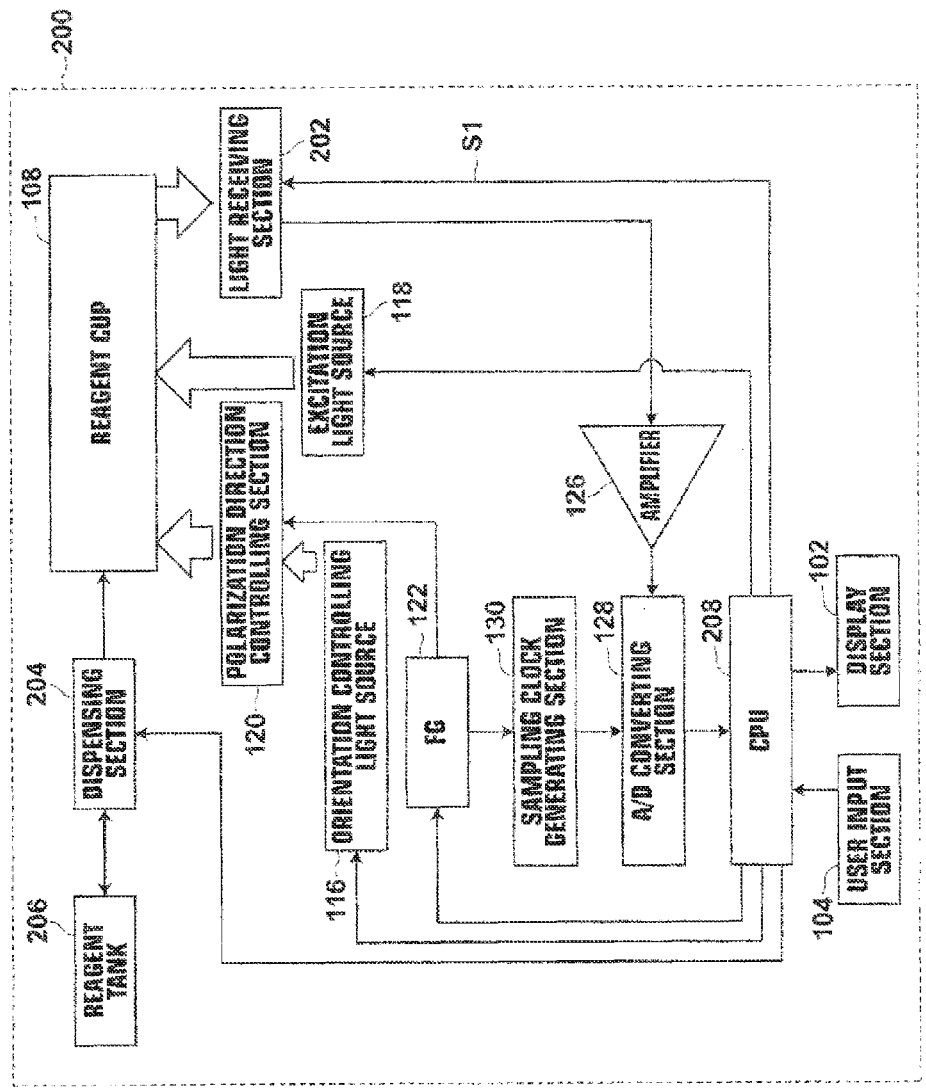
FIG. 14 is a block diagram that illustrates the main components of the biological molecule detecting apparatus according to the second embodiment.

FIG. 14 is a block diagram that illustrates the main components of the biological molecule detecting apparatus 200 according to the second embodiment. Note that constituent elements of the biological molecule detecting apparatus 200 which are the same as those of the biological molecule detecting apparatus 100 of the first embodiment are denoted with the same reference numerals, and detailed descriptions thereof will be omitted.

The biological molecule detecting apparatus 200 is different from the biological molecule detecting apparatus 100 of the first embodiment in the configurations of a light receiving section 202, a dispensing section 204, a reagent tank 206, and a CPU 208.

The dispensing section 204 suctions two types of antibodies from the reagent tank 206, which stores a plurality of antibodies in separate containers, and dispenses the suctioned antibodies into the reagent cup 108.

The light receiving section 202 detects fluorescence emitted by the fluorescent molecules within the reagent cup 108. The light receiving section 202 is configured to receive fluorescence emitted by the fluorescent molecules 40 and fluorescence emitted by the fluorescent molecules 42 separately in response to commands (S1) from the CPU 208.

The CPU 208 performs calculations on digital data output thereto from the A/D converting section 128, and outputs the results of calculation to the display section 102. In addition, the CPU 208 controls the operations of the orientation controlling light source 116, the excitation light source 118, the dispensing section 204, the FG 122, and the light receiving section 202 in response to commands input from the user input section 104. Specifically, the CPU 208 outputs ON/OFF commands to the orientation controlling light source 116 and the excitation light source 118, outputs commands that specify reagents to be utilized and commands to initiate dispensing operations to the dispensing section 204, outputs commands that specify the waveform of voltage signals to be output and commands to output the voltage signals to the FG 122, and outputs commands to switch filters to the light receiving section 202.

The configuration of the light receiving section 202 will be described in detail with reference to FIG. 15. FIG. 15 is a schematic diagram that illustrates the detailed structure of the light receiving section 202 of the biological molecule detecting apparatus 200 according to the second embodiment. A filter switching section 210 within the light receiving section 202 is equipped with two types of filters, a filter 212 and a filter 214. The two filters are movable, and the filter switching section 210 is configured to enable switching of the filter through which light focused the lens 142 passes. The filter switching section 210 switches the filter to be utilized in response to commands output thereto from the CPU 208. For example, the filter 212 is utilized in cases that fluorescence emitted by Alexa Fluor 568 is to be detected, and the filter 214 is utilized in cases that fluorescence emitted by Alexa Fluor 555 is to be detected. Thereby, unnecessary fluorescence is prevented from reaching the photodiode 150. In the present embodiment, a light receiving side filter of a SpRed-A filter set by Semrock is employed as the filter 212. The light receiving side filter of the SpRed-A filter set is a band pass filter that transmits wavelengths within a range from 605 nm to 650 nm. Meanwhile, a light receiving side filter of a SpOr-A filter set by Semrock is employed as the filter 214. The light receiving side filter of the SpOr-A filter set is a band pass filter that transmits wavelengths within a range from 575 nm to 600 nm. Note that in the present embodiment, two types of filters are employed to spectrally separate light to prevent unnecessary fluorescence from reaching the photodiode 150. However, it is not necessary to spectrally separate light using filters. For example, only light having specific wavelengths may be received by the photodiode, by spectrally separating light using a diffraction grating or a prism.

Next, the measurement operations of the biological molecule detecting apparatus 200 will be described. The measurement operations of the biological molecule detecting apparatus 200 are basically the same as the measurement operations of the biological molecule detecting apparatus 100 of the first embodiment, but differ in fine points. The principle behind detecting the free molecules and the binding molecules separately was described with respect to the first embodiment, and therefore how the two types of binding molecules are detected separately will be described here.

First, the biological molecule detecting apparatus 200 determines which of the two types of binding molecules are to be detected. This determination may be performed as desired, by user input via the user input section 104, for example. Here, a case will be described in which the binding molecules A having Alexa Fluor 568 as fluorescent molecules are detected first will be described. The CPU 208 outputs a command that instructs the filter switching section 210 within the light receiving section 202 to utilize the filter 212. The filter switching section 210 receives the command from the CPU 208, and moves the filter 212 to a position at which light focused by the lens 142 passes. When the orientation control signal is changed to 5V and excitation light is emitted toward the reagent cup 108, fluorescence is emitted by the fluorescent molecules 40 and the fluorescent molecules 42 within the solution. The fluorescence emitted by the fluorescent molecules 40 and the fluorescent molecules 42 is focused by the lens 142 and enters the filter 212. The filter 212 only transmits light having wavelengths within a range from 605 m to 650 nm. Therefore, the fluorescence emitted by the fluorescent molecules 40 passes through the filter 212, while the fluorescence emitted by the fluorescent molecules 42 is substantially completely shielded. Only the fluorescence emitted by the fluorescent molecules 40 can be detected in this manner.

Figure 16A:
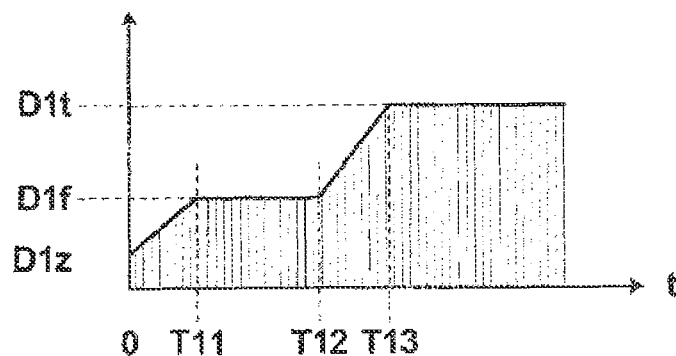
FIG. 16A is a graph that illustrates the output from an A/D converting section of the biological molecule detecting apparatus according to the second embodiment when a first detection target substance is detected.

The output of the A/D converting section resulting from performing a single measurement cycle with the biological molecule detecting apparatus 200 detecting the fluorescence emitted by the fluorescent molecules 40 in the same manner as in the first embodiment is illustrated in FIG. 16A. Note that here, the graph of FIG. 16A is illustrated schematically in order to simplify calculations.

The A/D converting section outputs a value D1z that represents a sum of the output due to the fluorescent molecules 40 which are bound to the two end surfaces of the orienting labels 8 of the free molecules A and the binding molecules A, when measurement is initiated. The value output by the A/D converting section gradually increases and becomes temporarily saturated at time T11 at a value D1f. Thereafter, the output of the A/D converting section begins to increase again at time T12, and becomes saturated again at time T13 at a value D1t.

The biological molecule detecting apparatus 200 switches the orientation control signal at predetermined temporal intervals to perform a plurality of cycles of measurements, calculates arithmetic means for a plurality of D1t values, D1f values, and D1z values, and obtains average values for each of the D1t values, D1f values, and D1z values.

Next, the CPU 208 calculates the concentration of the binding molecules A from the obtained average values for D1t, D1f, and D1z.

Specifically, the same calculation as that performed when obtaining the measurement value S in the first embodiment are performed to obtain a measurement value S1. Then, a calibration curve function f1(S) is employed to convert the measurement value S1 to a concentration C1. The CPU 208 outputs the obtained concentration C1 to the display section 102.

Next, the biological molecule detecting apparatus 200 performs measurement of the binding molecules B. The CPU 208 outputs a command that instructs the filter switching section 210 within the light receiving section 202 to utilize the filter 214. The filter switching section 210 receives the command from the CPU 208, and moves the filter 214 to a position at which light focused by the lens 142 passes. The filter 214 only transmits light having wavelengths within a range from 575 to 600 nm. Therefore, the fluorescence emitted by the fluorescent molecules 40 is shielded by the filter 214, while the fluorescence emitted by the fluorescent molecules 42 is transmitted therethrough. Only the fluorescence emitted by the fluorescent molecules 42 can be detected in this manner.

Figure 16B:
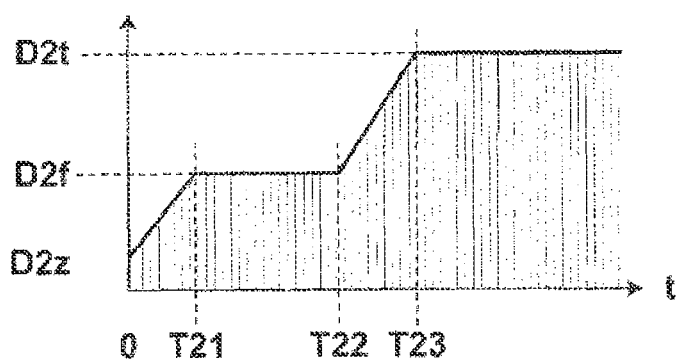
FIG. 16B is a graph that illustrates the output from the A/D converting section of the biological molecule detecting apparatus according to the second embodiment when a second detection target substance is detected.

The output of the A/D converting section resulting from performing a single measurement cycle with the biological molecule detecting apparatus 200 detecting the fluorescence emitted by the fluorescent molecules 42 is illustrated in FIG. 16B. Note that here, the graph of FIG. 16B is illustrated schematically in order to simplify calculations.

The A/D converting section outputs a value D2z that represents a sum of the output due to the fluorescent molecules 40 which are bound to the two end surfaces of the orienting labels 8 of the free molecules B and the binding molecules B, when measurement is initiated. The value output by the A/D converting section gradually increases and becomes temporarily saturated at time T21 at a value D2f. Thereafter, the output of the A/D converting section begins to increase again at time T22, and becomes saturated again at time T23 at a value D2t.

The biological molecule detecting apparatus 200 switches the orientation control signal at predetermined temporal intervals to perform a plurality of cycles of measurements, calculates arithmetic means for a plurality of D2t values, D2f values, and D2z values, and obtains average values for each of the D2t values, D2f values, and D2z values.

The timings at which the orientation control signals are switched when the binding molecules B are measured are different from those when the binding molecules A are measured. This is because the volumes and masses of the binding molecules A, the free molecules A, the binding molecules B, and the free molecules B are different, and the amounts of time required for orientation of the molecules to be completed differ.

As illustrated in FIGS. 16A and 16B, the timings at which the PD outputs increase and become saturated differ between the case that the binding molecules A are measured and the case that the binding molecules B are measured. This difference is due to the difference in the ease with which the binding molecules A and the binding molecules B move within the solution, caused by the difference in the volumes thereof.

Next, the CPU 208 calculates the concentration of the binding molecules B from the obtained average values for D2t, D2f, and D2z. Specifically, the same calculation as that performed when obtaining the measurement value S in the first embodiment are performed to obtain a measurement value S2. Then, a calibration curve function f2(S) is employed to convert the measurement value S2 to a concentration C2. The CPU 208 outputs the obtained concentration C2 to the display section 102.

As described above, the biological molecule detecting apparatus 200 according to the second embodiment of the present invention employs two types of antibodies and fluorescent molecules as substances that specifically bind with detection target substances and is equipped with the filter switching 210 which enables switching between two types of filters, in addition to having the structures of the biological molecule detecting apparatus 100 of the first embodiment. Thereby, only fluorescence emitted by the fluorescent molecules associated with the binding molecules that include a detection target substance can be detected, by utilizing a filter corresponding to the fluorescent molecules associated with the binding molecules that include the detection target substance. Accordingly, the concentrations of two types of detection target substances which are included in a single sample can be accurately measured.

Being able to measure a plurality of detection target substances from a single sample is important from the viewpoint of improving diagnostic accuracy.

Note that Alexa Fluoro 568 and Alexa Fluoro 555 were employed as the fluorescent molecules in the present embodiment. However, the fluorescent molecules are not limited to these. A plurality of substances that specifically bind to a plurality of detection target substances respectively may be labeled with a plurality of types of fluorescent molecules having fluorescent wavelengths which are sufficiently different to be capable of being separated by filters.

Note that the present embodiment was described as a case in which antigen antibody reactions are utilized as an example. However, the combination of the detection target substance and the substance that specifically binds with the detection target substance is not limited to the case described above. For example, the present invention may be applied to cases in which antigens are employed to detect antibodies, cases in which a specific nucleic acid is employed to detect a nucleic acid that hybridizes with the specific nucleic acid, cases in which nucleic acids are employed to detect nucleic acid binding proteins, cases in which ligands are employed to detect receptors, cases in which sugars are employed to detect lectin, cases in which protease detection is utilized, cases in which higher order structure changes are utilized, etc.

In addition, the present embodiment was described as a case in which two types of detection target substances are employed. However, the number of detection target substances is not limited to two. In such cases as well, each of the detection target substances can be detected separately, by employing a plurality of substances that specifically bind with each of the plurality of detection target substances, labeling each of the plurality of specific binding substances with a different type of fluorescent molecules, and detecting the fluorescence emitted by each type of fluorescent molecule by separating the fluorescence with a plurality of filters corresponding to each type of fluorescent molecule.

Note that the number of types of fluorescent molecules will increase as the number of types of detection target substances increases, and fluorescence emitted by the plurality of types of fluorescent molecules will be present, and there may be cases in which it is difficult to separate the fluorescence using only filters. In such cases, the types of excitation light may be increased to facilitate separate the fluorescence. The degrees of light absorption of fluorescent molecules depend on the wavelength of excitation light, and each type of fluorescent molecule has a wavelength band which is easily absorbed. For this reason, changing the wavelength of the excitation light causes only a portion of the fluorescent molecules to emit fluorescence, facilitating separation of the fluorescence using filters. In addition, detection of fluorescence emitted by target fluorescent molecules can be facilitated by employing band pass filters having narrower passbands.

Design Modifications to the First and the Second Embodiments

Note that the embodiments of the present invention described above are merely examples of the present invention, and do not limit the structure of the present invention. The biological molecule detecting apparatus of the present invention is not limited to the embodiments described above, and various changes and modifications are possible as long as they do not stray from the objective of the present invention.

For example, the external force applied to the molecules within the solution is not limited to that applied by laser beams. Magnetic methods or electric methods may be employed as long as they apply external force to a degree that causes differences in the amounts of time required for the reorientation of free molecules and binding molecules to become complete.

In addition, in the embodiments described above, the vibration direction of the orientation controlling light beam was switched between two directions perpendicular to each other, that is, that a direction parallel to the vibration direction of the excitation light, and a direction perpendicular to the vibration direction of the excitation light. However, it is not necessary for the two directions that the switch is performed between to be perpendicular to each other. The amounts of light emitted by each of the free molecules and each of the binding molecules will differ according to the orientation directions thereof, because the excitation efficiency of the fluorescent molecules of the free molecules and the binding molecules differ if the directions that they are oriented in are different. Accordingly, the fluorescence emitted by the free molecules and by the binding molecules can be separated and calculated, even if the orientation directions of the free molecules and the binding molecules are not two directions which are perpendicular to each other. In the case that two directions that the laser beam propagates in are perpendicular, the difference in the amounts of time required for orientation of the free molecules and the binding molecules to be completed becomes maximal, resulting in the highest S/N ratio. Meanwhile, if the angle formed by the two directions that the laser beam propagates in is 60 degrees, the amounts of time required for reorientation of the free molecules and the binding molecules to be completed will be shorter, and the amount of time required to perform measurements will also become shorter. In this manner, as the angle formed by the two directions that the laser beam propagates in decreases from 90 degrees, the amounts of time required for reorientation of the free molecules and the binding molecules to be completed will be shorter, and the amount of time required to perform measurements will also become shorter.

In addition, in the case that measurements are performed merely to ascertain whether a detection target substance is present within a solution, that is, whether binding molecules are present, it is only necessary to switch the emission direction of the laser beam into two directions having an angular difference that will cause a difference in the amounts of time required for reorientation of the free molecules and the binding molecules to be completed to occur. That is, it is not necessary for the two directions to include that which orients the direction of the transition moments of the fluorescent molecules associated with the free molecules and the binding molecules to be perpendicular to the vibration direction of the excitation light. If a difference is generated in the amounts of time required for orientation of the free molecules and the binding molecules to be completed, the difference will be represented in the fluorescence data, and therefore the presence of the binding molecules can be confirmed.

In addition, a $\lambda/2$ wavelength plate was employed in the embodiments of the present invention to switch the vibration direction of the orientation controlling light beam. However, it is not necessary to utilize the $\lambda/2$ wavelength plate. For example, a configuration that utilizes a mirror to change the vibration direction of the laser beam may be employed. As another alternative, two orientation controlling light sources 116 may be provided to emit laser beams from two directions.

Cases in which a single reagent cup is provided within the biological molecule detecting apparatus were described in the above embodiments. However, it is not necessary for a single reagent cup to be employed, and a configuration may be adopted in which a plurality of reagent cups, in which a plurality of samples are set, are provided in the biological molecule detecting apparatus. In this case, if the apparatus is configured to sequentially move the reagent cups to measurement positions and to perform measurements, a plurality of samples can be automatically measured.

Note that the above embodiments were described as cases in which antibodies labeled with fluorescent molecules were employed. However, it is not necessary to use antibodies which have already been labeled with fluorescent molecules. For example, binding of antibodies and antigens and binding of the antibodies and fluorescent molecules may be simultaneously performed within a reagent cup. In this case, a user may prepare antibodies and fluorescent molecules in separate reagent tanks, and the biological molecule detecting apparatus may dispense the antibodies, the fluorescent molecules, and a sample into a reagent cup, to cause reactions to occur when performing measurements.

In addition, the orientation controlling light source 116 and the excitation light source 118 may be configured to be removable, such that they may be replaced by those appropriate to a detection target substance and the type of fluorescent molecule.

If the detection target substance is detected or quantified by switching the direction in which orientation is controlled by the orientation control means at predetermined temporal intervals, and the arithmetic means of the plurality of pieces of obtained fluorescence data are calculated, the influence of noise that occurs within each measurement cycle can be reduced, and measurements can be performed with higher accuracy.

It is desirable for the temporal intervals at which the direction of orientation control to be switched to be determined by obtaining the amount of time required for orientation of all of the free molecules and all of the binding molecules to be completed, based on the mass or the volume of the detection target substance, the orienting labels, and the fluorescent molecules, and the degree of orientation control exerted by the orientation control means, and designating the obtained amount of time as the length of the temporal interval. In this case, the laser beam will not be emitted in the same direction after orientation of all of the molecules are completed, thereby reducing power consumption. In addition, measurement will not be continued extraneously, and measurement times can be shortened.

The amount of time required for orientation of all free molecules and all binding molecules to be completed may be obtained based on PD output or the output of the A/D converting section. For example, if several measurement cycles are repeated, the approximate amount of time required for the outputs to become saturated can be understood. Therefore, an arithmetic mean of the amounts of time required for the outputs to become saturated may be calculated, and the calculated amount of time may be designated as the predetermined temporal interval.

Complex mechanisms are obviated in the case that a laser beam is employed to control the orientations of molecules compared to a case that the orientations of molecules are controlled by magnets, etc. In order to control the orientations of molecules using magnets, for example, the molecules need to be magnetic, or magnetic molecules that bind with molecules of which the orientations are to be controlled need to be prepared, and preparations for measurements become complex.

Note that in the embodiments of the present invention, collagen was described as an example of the orienting label. However, it is not necessary for the orienting labels to be collagen. It is only necessary for the orienting labels to be a rod shaped substance which is capable of being oriented by light within a solution and capable of binding antigens and fluorescent molecules about the peripheries thereof. Examples of other orienting labels include actin filaments and metal nanorods (gold, silver, copper, ferric oxide, etc.), and plastics.

In addition, the length of the orienting labels in the longitudinal directions thereof need not be 300 nm, and any length may be adopted, as long as it is possible for a plurality of fluorescent molecules to be bound to the peripheries of the orienting labels.

Note that in the embodiments of the present invention, cases were described in which a single antibody was bound to each orienting label, in order to simplify the description. However, it is not necessary for the number of antibodies which are bound to the orienting labels to be 1.

Note that in the embodiments of the present invention described above, cases were described in which whole blood was employed as samples. However, the sample is not limited to being whole blood, and other bodily fluids such as urine and spinal fluid may be employed as samples as long as detection target substances are dispersed within solutions thereof.

In addition, the embodiments of the present invention can per form measurements in a liquid phase, in which antigens, antibodies, and fluorescent molecules are dispersed within a solution, and therefore exhibits the advantageous effect that preliminary processes are simple compared to solid phase measurements. In addition, there is another advantageous effect that reactions are faster than those in the case that the solid phase is employed, because the antigens and the free molecules can move freely within the solution.

In addition, the embodiments of the present invention do not detect changes in the degrees of fluorescent polarization due to changes in Brownian motion as in the conventional fluorescence polarization method. Therefore, even if fluorescence lifetimes are influenced by components within samples, the influence on measurements is small.

In addition, the number of orientation controlling light sources is not limited to one for each emission direction in the present invention. A plurality of orientation controlling light sources that emit a plurality of orientation controlling beams in a single direction may be provided.

The embodiments of the present invention were described as cases in which the excitation light 119, which is linearly polarized in a single direction, is emitted onto the solution. That is, the excitation light 119 has a single polarization plane. However, it is not necessary for the excitation light 119 to be a linearly polarized light beam having a single polarization plane. In order to obtain the same advantageous effects as those obtained by the first embodiment and the second embodiment, the excitation light 119 needs only to have at least one component which is linearly polarized in a specific direction. Here, light which is linearly polarized in a specific direction is light for which changes in the relationship between the transition moments of fluorescent molecules and the vibration direction of the linearly polarized component changes the excitation efficiency of the linearly polarized component with respect to the fluorescent molecules. For example, if randomly polarized excitation light may be emitted and an analyzer may provided in front of the light receiving section such that only components of fluorescence emitted from the fluorescent molecules which are linearly polarized in a specific direction is received. Here, randomly polarized light refers to light in which the vibration direction is random, and a plurality of linearly polarized components that vibrate in various directions are present.

FIG. 17A is a conceptual diagram that illustrates the orientation direction of a binding molecule 22 when an orientation controlling light beam 117 which is linearly polarized in a vibration direction 222 is emitted and when randomly polarized excitation light 230 is emitted. FIG. 17B is a conceptual diagram that illustrates the orientation direction of a binding molecule 22 when an orientation controlling light beam 117 which is linearly polarized in a vibration direction 224 is emitted and when randomly polarized excitation light 230 is emitted. Note that FIG. 17A is a diagram that illustrates a state in which the orientation control signal is 0V, FIG. 17B is a diagram that illustrates a state in which the orientation control signal is 5V. The vibration directions 232a through 232d of the excitation light 230 represent the vibration directions of light within a plane perpendicular to the direction in which the excitation light 230 propagates. In FIG. 17A and FIG. 17B, the vibration directions 232a through 232d illustrate that the excitation light 230 vibrates in various directions. It is known that generally, when fluorescent molecules which are static within a solution due to being oriented are excited by linearly polarized excitation light, the fluorescent molecules emit fluorescence which is polarized in the same direction as the vibration direction of the excitation light. When the fluorescent molecules 14 associated with the binding molecules 22 are excited by the randomly polarized excitation light 230, the fluorescent molecules 14 emit randomly polarized fluorescence 234.

An analyzer 236 transmits components of the randomly polarized fluorescence 234 emitted by the fluorescent molecules 14 that vibrate in a specific direction, and cut off components that vibrate in other directions. In other words, the only light that vibrates in the specific direction passes through the analyzer 236. The component of the fluorescence 234 that vibrates in the specific direction capable of passing through the analyzer 236 is a component which is excited by a component of the excitation light 230 which is linearly polarized in the vibration direction 232a. Accordingly, the vibration direction of the fluorescence 234 that passes through the analyzer 236 is only the vibration direction 232a in FIGS. 17A and 17B. Thereby, only the component of the fluorescence 234 emitted by the fluorescent molecules 14 which is excited by the component of the excitation light 230 which is linearly polarized in the vibration direction 232a reaches a photodiode 238. By adopting this configuration, the same measurements as those performed by the first embodiment can be performed with respect to light that vibrates in a specific direction, even if randomly polarized light is employed as the excitation light 230. Note that the component of the fluorescence 234 that vibrates in the specific direction transmitted by the analyzer 236 is not limited to the component that vibrates in the direction described here. A component that vibrates in any direction may be transmitted by the analyzer 236 as long as differences occur in the excitation efficiency of the fluorescent molecules 14 accompanying changes in the orientation direction thereof.

In addition, FIG. 17A and FIG. 17B illustrate examples in which the amplitude of vibration of the excitation light 230 is constant for all vibration directions. However, it is not necessary for the amplitude of vibration to be constant for all vibration directions. The component of the randomly polarized fluorescence 234 which is received by the photodiode 238 is only that which vibrates in the specific direction, and therefore components that vibrate in other directions are cut off.

As illustrated in FIG. 17A, when the orientation control signal is 0V, the vibration direction 222 of the orientation controlling light beam 117 is parallel to the vibration direction of light which can be transmitted through the analyzer 236. At this time, the longitudinal directions of the orienting labels 8 are parallel to the vibration direction of light which can be transmitted through the analyzer 236. Accordingly, the transition moments of the majority of the fluorescent molecules 14 (mainly the fluorescent molecules 14 which are bound to the lateral surfaces of the orienting labels 8) associated with the binding molecules 22 which have been oriented by the orientation controlling light beam 117 which is linearly polarized in the vibration direction 222 and the vibration direction 232a of light that can be transmitted through the analyzer 236 are perpendicular to each other. That is, the majority of the fluorescent molecules 14 associated with the binding molecules 22 are not excited by the component of the excitation light 230 that vibrates in the vibration direction 232a. In other words, the excitation efficiency of the binding molecules 22 with respect to the component of the excitation light 230 that vibrates in the vibration direction 232a is minimal. Accordingly, output of the photodiode 238 is minimal, because the component of the fluorescence 234 emitted by the binding molecules 22 that passes through the analyzer 236 is that which is emitted by being excited by the component of the excitation light 230 that vibrates in the vibration direction 232a.

In contrast, as illustrated in FIG. 17B, when the orientation control signal is 5V, the vibration direction 224 of the orientation controlling light beam 117 is perpendicular to the vibration direction of light which can be transmitted through the analyzer 236. At this time, the longitudinal directions of the orienting labels 8 are perpendicular to the vibration direction of light which can be transmitted through the analyzer 236. Accordingly, the transition moments of the fluorescent molecules 14 which are bound to the lateral surfaces of the orienting labels 8 associated with the binding molecules 22 which have been oriented by the orientation controlling light beam 117 which is linearly polarized in the vibration direction 224 and the vibration direction of light that can be transmitted through the analyzer 236 are parallel to each other. In this case, the excitation efficiency of the binding molecules 22 with respect to the component of the excitation light 230 that vibrates in the vibration direction 232a is maximal. That is, the component of the fluorescence 234 that passes through the analyzer 236 is maximal, and the output of the photodiode 238 also becomes maximal.

In the case that such a configuration is adopted as well, the orientation directions of the fluorescent molecules 14 will change when the orientation control signal is switched from 0V to 5V, and the directions of the transition moments of the fluorescent molecules and the vibration direction of light which is transmitted through the analyzer 236 gradually become parallel. Accompanying this gradual approach to becoming parallel, the excitation efficiency of the fluorescent molecules 14 with respect to the component of the excitation light 230 that vibrates in the direction which is capable of being transmitted through the analyzer 236 increases. The increase in excitation efficiency results in an increase of the intensity of the component of the fluorescence 234 emitted by the fluorescent molecules 14 that vibrates in the direction which is capable of being transmitted through the analyzer 236. That is, the intensity of fluorescence detected by the photodiode 238 gradually increases. Here, a description was given with respect to the binding molecules 22. However, the same can be said in the case that randomly polarized excitation light is emitted onto free molecules as well. In this case, the amounts of time required for orientation of the free molecules and the binding molecules to be completed differ, and therefore the timings at which the intensity of fluorescence received by the photodiode 238 increasing and becoming saturated will differ. Therefore, the timings at which the intensity of fluorescence increase and become saturated will differ. For this reason, a graph that represents the output of the photodiode 238 over time when the orientation control signal is switched from 0V to 5V will have the same shape as the graph of FIG. 11, even in the case that the configuration described above is adopted. That is, in this case as well, the concentration of the detection target substance can be measured by performing the same calculations as those performed in the first embodiment with respect to the graph representing the output of the photodiode 238.

Figure 18A:
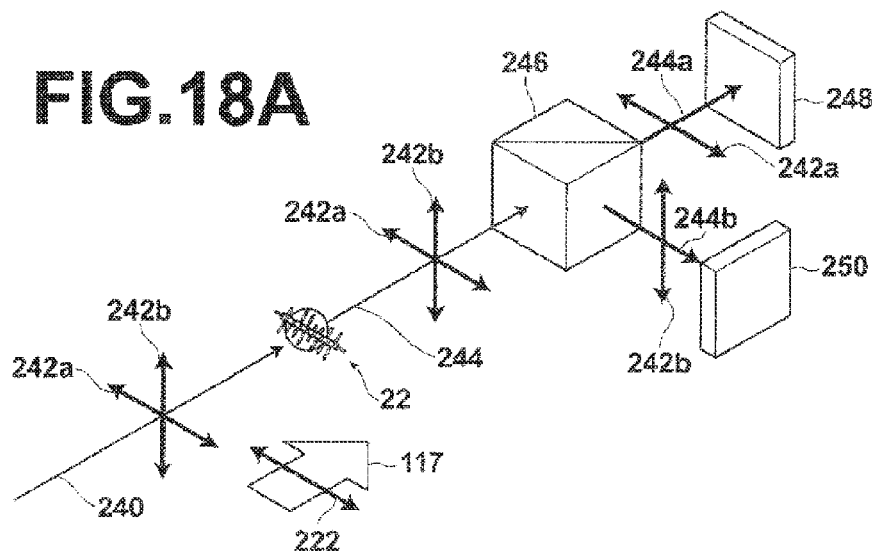
FIG. 18A is a conceptual diagram that illustrates the relationship between the transition moment of a fluorescent molecule and the vibration direction of excitation light which is linearly polarized in two directions in the case that a laser beam is emitted from a first direction.
Figure 18B:
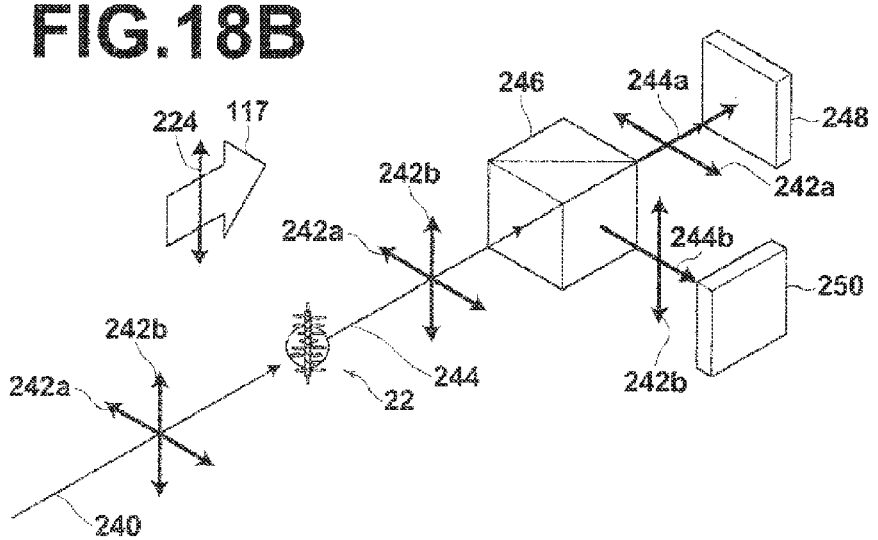
FIG. 18B is a conceptual diagram that illustrates the relationship between the transition moment of a fluorescent molecule and the vibration direction of excitation light which is linearly polarized in two directions in the case that a laser beam is emitted from a second direction.

As a further alternative, excitation light 240 that consists of two components which are linearly polarized in two directions perpendicular to each other may be employed, as illustrated in the conceptual diagrams of FIG. 18A and FIG. 18B. The excitation light 240 only has two components, which are linearly polarized in vibration directions 242a and 242b within a plane perpendicular to the direction in which the excitation light 240 propagates. That is, the vibration direction 242a and the vibration direction 242b are perpendicular to each other. The fluorescent molecules 14 which are excited by the excitation light 240 emit fluorescence 244 having components that vibrate in the same vibration directions as those of the excitation light 240. That is, fluorescence 244 has two components which are linearly polarized in the vibration directions 242a and 242b.

FIG. 18A is a conceptual diagram that illustrates a case in which an orientation control signal is 0V. When the orientation control signal is 0V, orientation controlling light beam 117 which is linearly polarized in the vibration direction 222 is emitted. The transition moments of the fluorescent molecules 14 of the binding molecules (mainly the fluorescent molecules 14 which are bound to the lateral surfaces of the orienting labels 8) which are oriented by the orientation controlling light beam 117 linearly polarized in the vibration direction 222 are oriented in a direction perpendicular to the vibration direction 242a. That is, in the case that the orientation control signal is 0V, the excitation efficiency of the binding molecules 22 with respect to the component of the excitation light 240 that vibrates in the vibration direction 242a becomes minimal. In contrast, the excitation efficiency of the binding molecules 22 with respect to the component of the excitation light 240 that vibrates in the vibration direction 242b becomes maximal.

A polarizing beam splitter 246 transmits a linearly polarized component 244a of the fluorescence 244 that vibrates in the vibration direction 242a, and reflects a linearly polarized component 244b of the fluorescence 244 that vibrates in the vibration direction 242b. The linearly polarized component 244a that passes through the polarizing beam splitter 246 reaches a photodiode 248. The linearly polarized component 244b which is reflected by the polarizing beam splitter 246 reaches a photodiode 250. In the case that the orientation control signal is 0V, the excitation efficiency of the binding molecules 22 with respect to the component of the excitation light 240 that vibrates in the vibration direction 242a becomes minimal. Therefore, the component that vibrates in the vibration direction 242a within the fluorescence 244 emitted by the binding molecules 22 becomes minimal, and the output of the photodiode 248 becomes minimal. In contrast, the output of the photodiode 250 becomes maximal.

FIG. 18B is a conceptual diagram that illustrates a case in which an orientation control signal is 5V. When the orientation control signal is 0V, orientation controlling light beam 117 which is linearly polarized in the vibration direction 224 is emitted. The transition moments of the fluorescent molecules 14 of the binding molecules (mainly the fluoresc molecules 14 which are bound to the lateral surfaces of the orienting labels 8) which are oriented by the orientation controlling light beam 117 linearly polarized in the vibration direction 222 are oriented in a direction perpendicular to the vibration direction 242b. That is, the excitation efficiency of the binding molecules 22 with respect to the component of the excitation light 240 that vibrates in the vibration direction 242b becomes minimal. In contrast, the excitation efficiency of the binding molecules 22 with respect to the component of the excitation light 240 that vibrates in the vibration direction 242a becomes maximal.

FIG. 19 is a collection of graphs having the voltage of an orientation control signal, the output of the photodiode 248, the output of the photodiode 250 and normalized output of the photodiodes as vertical axes, respectively, and time t as the horizontal axes. Note that here, the outputs of the photodiodes are illustrated schematically in the graphs in order to simplify the description.

In FIG. 19, the orientation control signal is set to 0V prior to measurement in the same manner as in the first embodiment. Prior to measurement, the orientation controlling light beam 117 which is linearly polarized in the vibration direction 222 is irradiated within the solution in the reagent cup, to orient the free molecules and the binding molecules in a single direction. The orientation controlling light beam 117 which is linearly polarized in the vibration direction 222 is switched to the orientation controlling light beam 117 which is linearly polarized in the vibration direction 224 accompanying initiation of measurement.

The linearly polarized component 244a of the fluorescence 244 that passes through the polarizing beam splitter 246 will be focused on. In this case, the relationship between the vibrating direction 242a of one of the components of the excitation light 240 and the direction of the transition moments of the fluorescent molecules 14 is the same as in the case of the first embodiment. Temporal changes in the output of the photodiode 248 are similar to those indicated in the graph of FIG. 11, which was described with respect to the first embodiment. That is, the orientation directions of the free molecules begin to change accompanying the switch in the vibration direction of the orientation controlling light beam 117 at time T31, and the output of the photodiode 248 increases from an initial value Iz3. The output of the photodiode 248 becomes a value if3 at time T32 after reorientation of the free molecules is complete, and remains constant for a period of time thereafter. Then, the output of the photodiode 248 increases again at time T33, when reorientation of the binding molecules begins. Thereafter, the output of the photodiode 248 becomes a maximal value it3 at time T34, when the reorientation of the binding molecules is complete. The orientation control signal is reset to 0V after maintaining an output of 5V for T seconds. When the orientation control signal is switched from 5V to 0V, the output of the photodiode 248 remains at the value iz3 for a period of time, and then decreases to the value iz3.

The linearly polarized component 244b of the fluorescence 244 which is reflected by the polarizing beam splitter 246 will be focused on. In this case, the vibrating direction 242b of the other one of the components of the excitation light 240 and the direction of the transition moments of the fluorescent molecules 14 is parallel until time T31. Therefore, the excitation efficiency of the fluorescent molecules 14 with respect to the other component of the excitation light 240 is maximal until time T31. That is, the intensity of the linearly polarized component 244b of the fluorescence 244 is maximal until time T31, and therefore the output of the photodiode 250 that receives the linearly polarized component 244b of the fluorescence 244 reflected by the polarizing beam splitter 246 is also maximal until time T31. The orientation directions of the free molecules begin to change accompanying the switch in the vibration direction of the orientation controlling light beam 117 at a time T31, and the output of the photodiode 250 decreases from an initial value it4. The output of the photodiode 250 becomes a value if4 at time T32 after reorientation of the free molecules is complete, and remains constant for a period of time thereafter. Then, the output of the photodiode 250 decreases again at time T33, when reorientation of the binding molecules begins. Thereafter, the output of the photodiode 250 becomes a minimal value iz4 at time T34, when the orientation of the binding molecules is complete. The orientation control signal is reset to 0V after maintaining a voltage of 5V for T seconds. When the orientation control signal is switched from 5V to 0V, the output of the photodiode 250 remains at the value iz4 for a period of time, and then increases to the value it4. This is because the vibration direction 242b of the other component of the excitation light 240 and the directions of the transition moments of the fluorescent molecules 14 return to being in a parallel state.

The CPU designates the output of the photodiode 248 as Pp and the output of the photodiode 250 to Pv, and normalizes these values according to Formula (3) below.

$$K=(Pp-Pv)/(Pp+Pv) \quad (3)$$

The influence of fluctuations in the concentrations of the free molecules and the binding molecules and fluctuations in the excitation power of the optical systems can be reduced, by normalizing the outputs of the two photodiodes in this manner.

Then, the concentration of the binding molecules is calculated from the graph of the normalized output of the photodiodes. Specifically, a measurement value S3 is obtained by Formula (4) below.

$$S3=(it5-if5)/(it5-iz5) \quad (4)$$

A calibration curve function is employed in the same manner as in the first embodiment, to obtain a diagnosis value C3 (the concentration of the detection target substance) from the obtained measurement value S3.

Figure 20A:
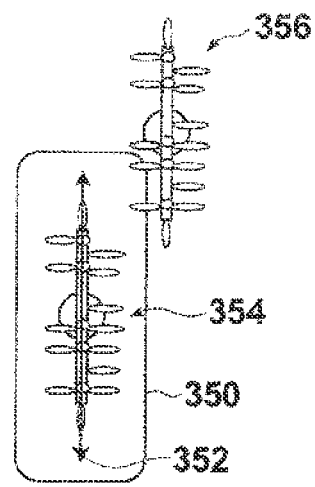
FIG. 20A is a first conceptual diagram for explaining changes in the orientation of a binding molecule accompanying changes in the polarization axis of a laser beam.

In the case that the directions of the transition moments of the fluorescent molecules are controlled by controlling the vibration direction of the linearly polarized orientation controlling light beam, the orientation controlling light beam may be of any cross sectional shape within a plane perpendicular to the propagation direction thereof. For example, a case will be considered in which a linearly polarized orientation controlling light beam 350 having a polarization axis 352 is emitted, as illustrated in FIG. 20A. In this case, the orientation controlling light beam 350 has a substantially rectangular cross sectional shape in a direction perpendicular to the propagation direction thereof. The motions of a binding molecule 354 positioned at the center of the orientation controlling light beam 350 and a binding molecule 356 positioned at the peripheral portion of the orientation controlling light beam 350 will be considered.

Figure 20B:
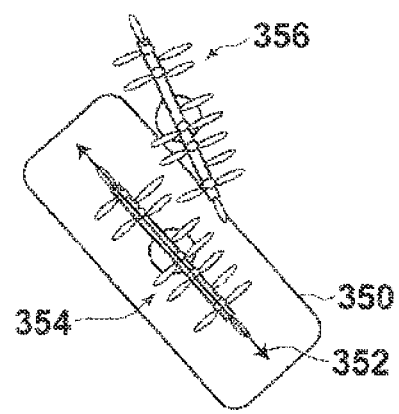
FIG. 20B is a second conceptual diagram for explaining changes in the orientation of a binding molecule accompanying changes in the polarization axis of a laser beam.

As illustrated in FIG. 20B, the polarization axis 352 rotates when the orientation controlling light beam 350 is rotated.

Figure 20C:
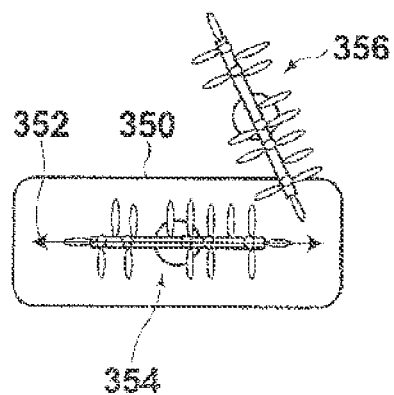
FIG. 20C is a third conceptual diagram for explaining changes in the orientation of a binding molecule accompanying changes in the polarization axis of a laser beam.

The binding molecule 354 which is positioned on the rotational axis (the center of rotation of the polarization axis 352) immediately tracks the rotation of the polarization axis 352, and rotates. Meanwhile, the binding molecule 356 positioned at the peripheral portion of the orientation controlling light beam 350 cannot track the rotation of the polarization axis 352 immediately, and becomes separated therefrom. After a period of time, the binding molecule 356 is also drawn into the orientation controlling light beam 350, and initiates rotation that tracks the rotation of the polarization axis 352. In the case that the polarization axis 352 of the orientation controlling light beam 350 is rotated 90 degrees from the polarization axis 352 of FIG. 20A as illustrated in FIG. 20C, the reorientation of the binding molecule 354 is completed simultaneously with the completion of rotation of the polarization axis 352. Meanwhile, because the binding molecule 356 cannot track the rotation of the polarization axis 352 immediately, reorientation of the binding molecule 356 is completed after a period of time following completion of rotation of the polarization axis 352. That is, the movement of the binding molecule 354 positioned on the rotational axis is rotation which is synchronized with the rotation of the polarization axis 352 of the orientation controlling light beam 350. However, the movement of the binding molecule 356 positioned at the peripheral portion of the orientation controlling light beam 350 is revolution about the rotational axis which is not synchronized with the rotation of the polarization axis 352 of the orientation controlling light beam 350.

Figure 21:
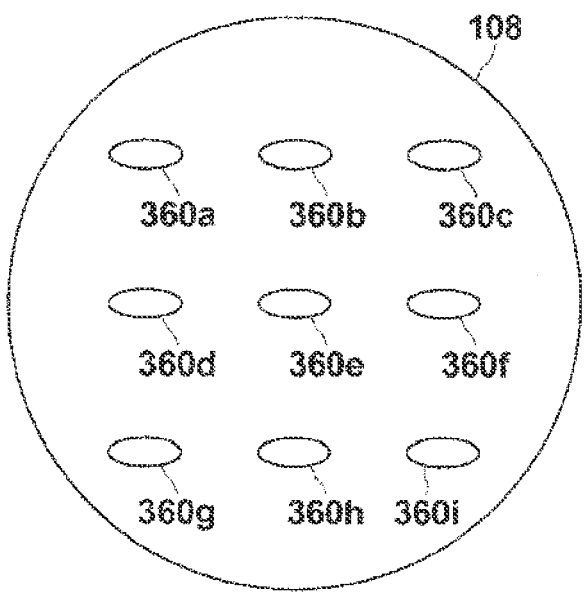
FIG. 21 is a conceptual diagram that illustrates a case in which linearly polarized laser beams are emitted onto a plurality of points in a reagent cup from the bottom surface thereof.

There are cases in which the presence of binding molecules that cannot track the rotation of the polarization axis 352 of the orientation controlling light beam 350 will influence measurements. In order to reduce such influence, it is preferable for the orientation controlling light beam to simultaneously enter a plurality of points from a predetermined direction. For example, as illustrated in FIG. 21 (a plan view of the reagent cup 108), a configuration may be adopted, in which nine laser beams corresponding to nine points 360a through 360i enter the reagent cup 108. By adopting such a configuration, the number of binding molecules which are positioned at the center of the polarization axes of the laser beams will increase, thereby reducing the aforementioned influence on measurements. Note that although an example in which laser beams enter nine points is described here, the number of points that the laser beams enter is not limited to nine, and may be greater than or less than nine. It is desirable for laser beams to enter a greater number of points the narrower that they are focused. Thereby, the binding molecules can be caused to rotate in synchrony with the rotation of the laser beams. As a result, sudden variations in fluorescent intensity can be reduced, and the coefficient of variation, which is an index that represents relative spreading, can be improved.

Figure 22:
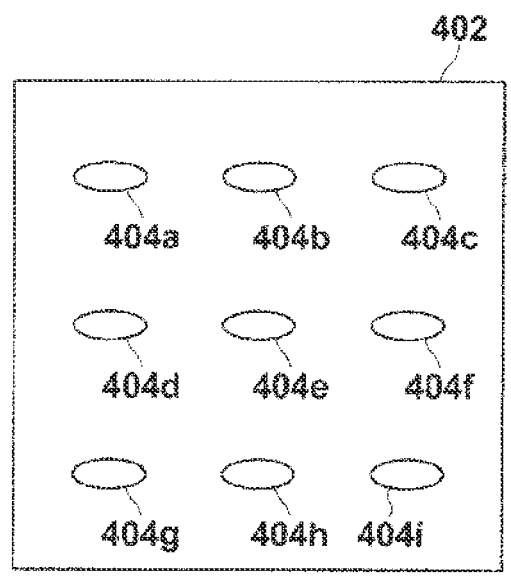
FIG. 22 is a conceptual diagram that illustrates the structure of an orientation controlling light source for casing linearly polarized laser beams to be emitted onto a plurality of points from a predetermined direction.

The structure of an orientation controlling light source 402 that causes orientation controlling light beams to simultaneous enter a plurality of points from a predetermined direction is illustrated in FIG. 22. The orientation controlling light source 402 is a 3.3 two dimensional laser array. Nine light emitting points 404a through 404i of the orientation controlling light source 402 emit light. The light emitting points have heights of 1 μm and widths of 100 μm. The distances among the light emitting points are approximately 100 μm.

An example of an optical system that employs the orientation controlling light source 402 of FIG. 22 is illustrated in FIG. 23. Note that structural elements other than the optical systems for laser beams and excitation light are omitted in FIG. 23.

Linearly polarized orientation controlling light beams 422 output from the orientation controlling light source 402 pass through a collimating lens 406 and become collimated light beams at a focal point. The orientation controlling light beams 422 which have passed through the collimating lens 406 pass through beam expanders 408 and 410, then enter a λ/2 wavelength plate 412. The orientation controlling light beams 422 which have passed through the beam expanders 408 and 410 are spread to become a collimated light beam having a specific magnification ratio. The λ/2 wavelength plate 412 is on a rotatable stage, and is configured to be rotatable. This configuration enables the vibration direction of the orientation controlling light beams 422 to be rotated. The orientation controlling light beams 422 which have passed through the λ/2 wavelength plate are reflected by a dichroic mirror 418, focused by a lens 420, enter the reagent cup 108 through the bottom surface thereof, and propagate upward.

Excitation light 424 output from a light source 414 passes through a lens 426 and is reflected by a dichroic mirror 416. The excitation light 424 which has been reflected by the dichroic mirror 416 passes through a dichroic mirror 418, is focused by a lens 420, enters the reagent cup 108 through the bottom surface thereof, and propagates upward.

If the focal distance of the collimating lens 406 is set to be 3.1 mm, and the focal distance of the lens 420 is set to be 4 mm in the optical system illustrated in FIG. 23, the magnification ratio will be 1.29×. Therefore, the sizes of the orientation controlling light beams 422 are approximately 1.3 μm·130 μm with pitches of approximately 129 μm at the bottom surface of the reagent cup 108.

Another example of an optical system that causes orientation controlling light beams to simultaneously enter a plurality of points from a predetermined direction will be described with reference to FIG. 24. Note that structural elements other than the optical systems for the orientation controlling beams and excitation light are omitted in FIG. 24. In addition, structural elements which are the same as those illustrated in FIG. 23 are denoted by the same reference numerals, and detailed descriptions thereof will be omitted.

Figure 25:
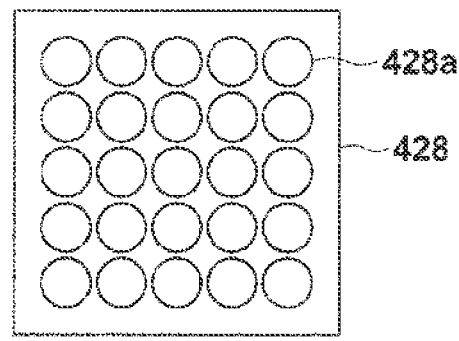
FIG. 25 is a conceptual diagram that illustrates a microlens array.

In the optical system illustrated in FIG. 24, the orientation controlling light source 116 is the same as that of the first embodiment. An orientation controlling light beam 432 passes through the collimating lens 406, the beam expanders 408 and 410, and enters a microlens array 428. As illustrated in FIG. 25, the microlens array 428 has a plurality of microlenses 428a arrayed in a lattice shape. The orientation controlling light beam 432 which passes through the microlens array 428 becomes a plurality of light beams which have different focal points, as light emitted by a plurality of light sources. The orientation controlling light beam 432 is focused by a pinhole array 430, reflected by the dichroic mirror 418, focused by the lens 420, enters the reagent cup 108 through the bottom surface thereof, and propagates upward. Laser beams can be caused to simultaneously enter a plurality of points from a predetermined direction by employing a microlens array in this manner as well.

Examples in which the λ/2 wavelength plate 412 is employed to change the vibration direction were described. Alternatively, a liquid crystal phase modulating device which is controlled by electrical signals may be employed to change the vibration direction.

Figure 26:
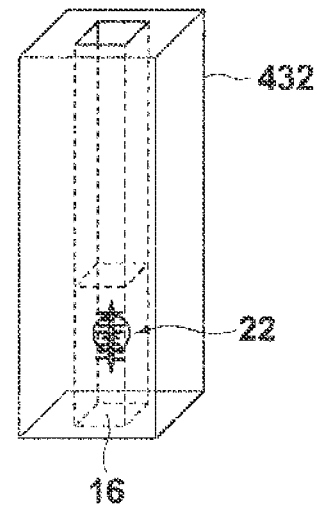
FIG. 26 is a conceptual diagram that illustrates an example of the shape of a reagent cup.

In addition, the reagent cup was of a cylindrical shape in the embodiments described above. However, it is not necessary for the shape of the reagent cup to be cylindrical. For example, a reagent cup 432 shaped as a rectangular column and having a rectangular columnar solution portion therein may be employed, as illustrated in FIG. 26. The reagent cup 432 having the rectangular columnar solution portion is particularly suited in cases that pressure applied by the orientation controlling light beam in the propagation direction thereof is utilized to press the free molecules and the binding molecules against the surface of an inner wall of the reagent cup 432. This is a phenomenon that occurs in cases that the masses of the free molecules and the binding molecules are light, caused by the free molecules and the binding molecules moving through the solution under the pressure applied by the orientation controlling light beam. In this case, if the solution holding portion is a rectangular column, the free molecules and the binding molecules are oriented while being pressed against the interface between the solution and the reagent cup 432. In the case that the interface is a flat surface and the pressure applied by the orientation controlling light beam operates in a direction perpendicular to the interface, the free molecules and the binding molecules will not move outside the irradiation range of the orientation controlling light beam by moving in directions parallel to the interface.

Figure 27:
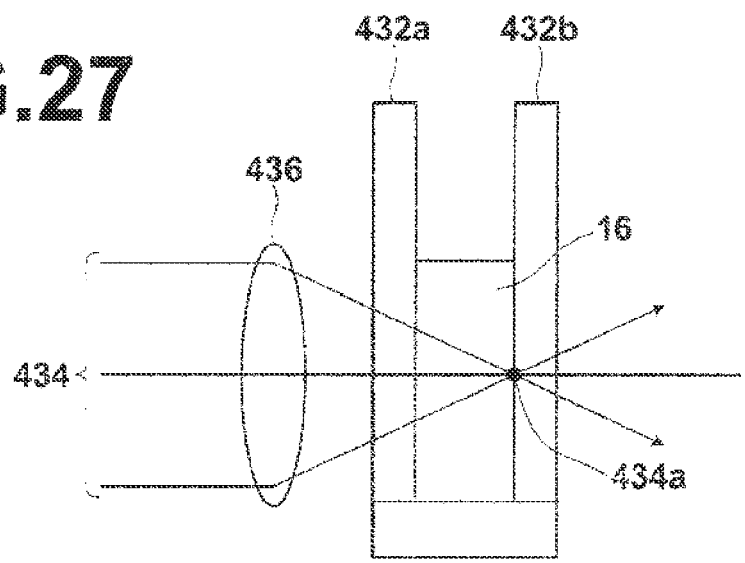
FIG. 27 is a conceptual diagram that illustrates an example of the positional relationship between the focal point of a focused laser beam and a reagent cup.

In addition, in the case that the free molecules and the binding molecules are pressed against the surface of the inner wall of the reagent cup 432, the molecules can be more easily oriented by setting the position of the focal point of the laser beam. FIG. 27 is a diagram that illustrates the positional relationship between the focal point of a focused orientation controlling light beam and a reagent cup. A orientation controlling light beams 434 enters a lens 436 and is focused at a focal point 434*a* at the interface between the plasma 16 and a side wall 432*b* (the inner surface of the side wall 432*b*). The intensity of the laser 434 is greatest at the position of the focal point 434*a*, and therefore the free molecules and the binding molecules can be pressed with a great amount of pressure. Accordingly, if the laser 434 is emitted in the manner illustrated in FIG. 27, the free molecules and the binding molecules can be more efficiently oriented while pressing the free molecules and the binding molecules against the inner surface of the side wall 432*b*. In this case as well, the orientation directions of the free molecules and the binding molecules can be changed at the position of the focal point 434*a* by rotating the vibration direction of the linearly polarized orientation controlling light beams 434.

Note that it is not necessary for the solution holding portion to be shaped as a rectangular column, and the solution holding portion needs only to have at least one flat surface. If an orientation controlling light beam is emitted such that it is focused at a focal point on the flat surface, the free molecules and the binding molecules will not move outside the irradiation range of the orientation controlling light beam by moving in directions parallel to the flat surface, and will be oriented while being pressed against the flat surface.

The embodiments of the present invention were described as cases in which the vibration direction of a linearly polarized orientation controlling light beam as controlled to control the orientation states of free molecules and binding molecules, thereby controlling the directions of the transition moments of the fluorescent molecules associated with the free molecules and the binding molecules. However, the method by which the directions of the transition moments of the fluorescent molecules are controlled is not limited to this method. For example, the direction in which the orientation controlling light beam is emitted with respect to the reagent cup may be switched to control the directions of the transition moments of the fluorescent molecules, utilizing the fact that the orientation states of molecules irradiated by light change according to the emission direction of the light. In this case, it is not necessary for the orientation controlling light beam to be polarized.

Figure 28:
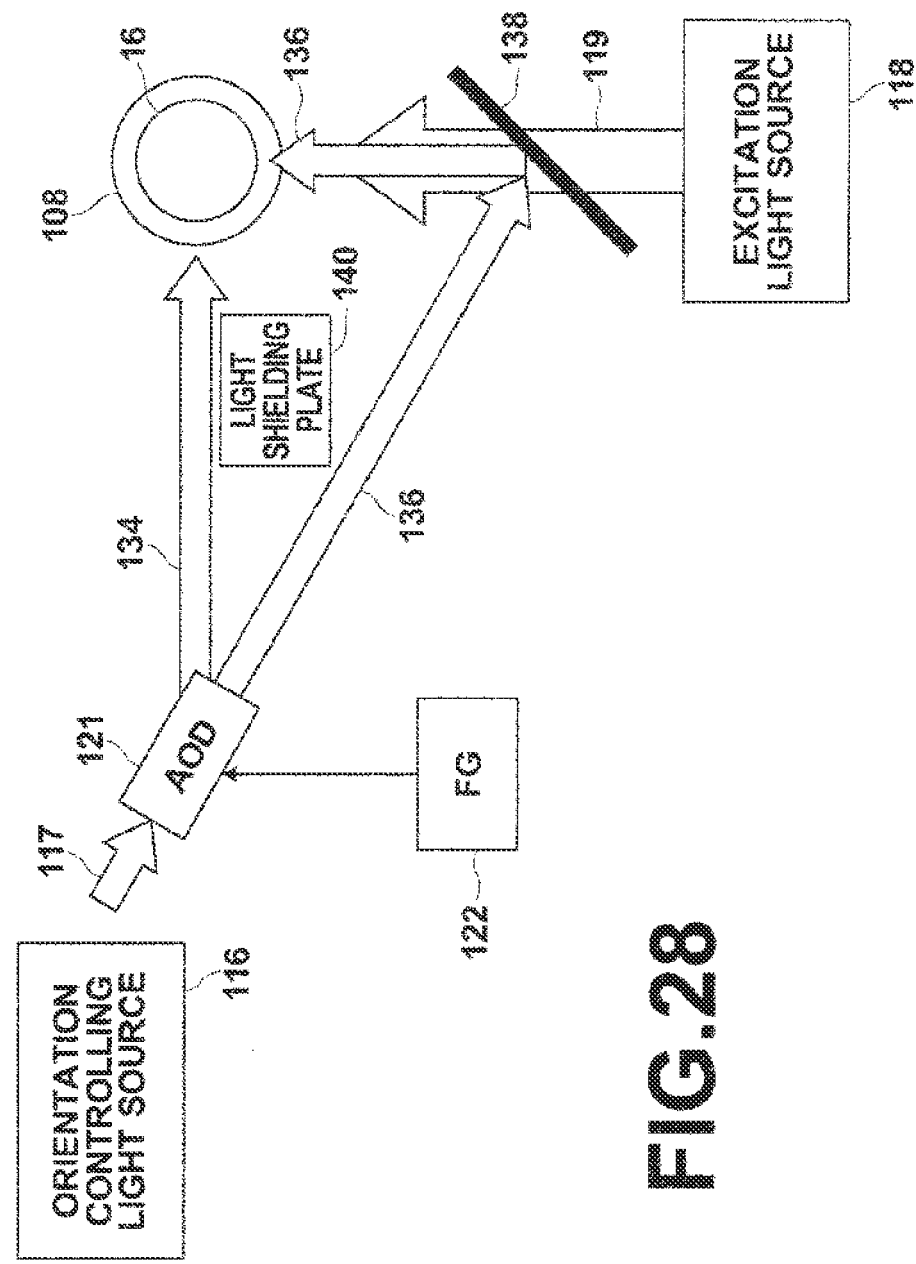
FIG. 28 is a conceptual diagram that illustrates an optical system for controlling the transition moments of fluorescent molecules by switching the emission direction of an orientation controlling light beam with respect to a reagent cup.

A method by which the emission direction of the orientation controlling light beam 117 with respect to the reagent cup 108 is switched to control the directions of the transition moments of fluorescent molecules will be described in greater detail with reference to FIG. 28. FIG. 28 is a schematic view that illustrates an optical system that switches the emission direction of the orientation controlling light beam 117 emitted from the orientation controlling light source 116 with respect to the reagent cup 108, in plan view (from the side of the opening of the cup). The orientation controlling light beam 117 emitted from the orientation controlling light source 116 passes through an AOD (Acousto Optical Deflector) 121 and enters the reagent cup 108. The orientation controlling light beam 117 emitted by the orientation controlling light source 116 is of a width that enables the entirety of the solution within the reagent cup 108 to be irradiated thereby. The AOD 121 alternately switches the direction that the orientation controlling light beam 117 emitted from the orientation controlling light source 116 propagates between two directions. Specifically, the AOD 121 causes the orientation controlling light beam 117 to propagate in the direction of the arrow 134 in the case that a 5V orientation control signal is input thereto, and causes the orientation controlling light beam 117 to propagate in the direction of the arrow 136 in the case that a 0V orientation control signal is input thereto. An orientation controlling light beam 134 enters the side surface of the reagent cup 108. An orientation controlling light beam 117 that propagates in the direction of the arrow 136 is reflected by the dichroic mirror 138, propagates in a direction perpendicular to the orientation controlling light beam 134, and enters the side surface of the reagent cup 108. If the reagent cup 108 viewed from above is considered as a clock face, the orientation controlling light beam 134 enters from the 9 o'clock position and propagates toward the 3 o'clock position, whereas the orientation controlling light beam 136 enters from the 6 o'clock position and propagates toward the 12 o'clock position. That is, the direction in which the orientation controlling light beam 134 propagates and the direction in which the orientation controlling light beam 136 propagates are perpendicular to each other. The dichroic mirror 138 only reflects light having the wavelength of the orientation controlling light beam 117, and transmits light having other wavelengths. The excitation light 119 emitted from the excitation light source 118 passes through the dichroic mirror 138, propagates in the same direction as the orientation controlling light beam 136 reflected by the dichroic mirror 138, and enters the side surface of the reagent cup 108.

This configuration enables the biological molecule detecting apparatus 100 to alternately switch the direction in which the laser beam enters the reagent cup 108 between two directions which are 90 degrees different from each other, by controlling the AOD 121 according to the input of the orientation control signals from the FG 122. A light shielding plate 140 is placed between the AOD 121 and the reagent cup 108, and the biological molecule detecting apparatus 100 is configured such that orientation controlling light beams that propagate in directions other than those indicated by the arrow 134 and the arrow 136 do not enter the reagent cup 108. In addition, the orientation controlling light beam 117 enters the side surface of the cylindrical reagent cup 108 both in the case that it propagates in the direction of the orientation controlling light beam 134 and in the direction of the orientation controlling light beam 136. Because the reagent cup 108 is cylindrical, the shape of the side surface of the reagent cup 108 that the orientation controlling light beam enters is the same even if the direction that the laser propagates in is switched.

In optical systems that control the directions of the transition moments of fluorescent molecules by changing the direction in which an orientation controlling light beam is emitted, a plurality of optical systems that simultaneously emit orientation controlling light beams toward a plurality of points from a certain direction may be provided to broaden the irradiation range of the orientation controlling light beams, in order to avoid a problem that the range that the orientation controlling light beam can irradiated will become small in cases that the orientation controlling light beam is focused into a narrow range. The plurality of optical systems may have a plurality of optical paths at least at a stage prior to the laser beam entering the reagent cup. For example, if three optical systems that also include light sources are provided, external force imparting light beams are emitted from all three external force imparting light sources, and the external force imparting light beams can irradiate three points of the reagent cup from a certain direction. As another example, a single external force imparting light beam may be branched by employing a two dimensional laser array, a microlens array, etc, and the external force imparting light beams can be emitted onto a plurality of points corresponding to the number of branches, even if only a single light source is provided. In such a case, the orientation controlling light beam can be simultaneously emitted onto a plurality of points, and the transition moments of the fluorescent molecules can be rotated at a plurality of locations.

FIELD OF INDUSTRIAL APPLICABILITY

The biological molecule detecting apparatus and the biological molecule detecting method of the present invention may be utilized in apparatuses that detect or quantify detection target substances by utilizing interactions between the detection target substances and substances that specifically bind to the detection target substances.

What is claimed is:

1. A biological molecule detecting method, comprising the steps of:
    emitting excitation light, having a linearly polarized component polarized in a specific direction, to excite fluorescent molecules within a solution;
    detecting first fluorescence emitted by a first complex constituted by a substance that specifically binds with a detection target substance, an orienting label, and a plurality of the fluorescent molecules which are bound to the periphery of the orienting label;
    detecting second fluorescence emitted by a second complex constituted by the first complex which is bound to the detection target substance;
    switching the orientations of the first complex and the second complex in at least two directions;
    detecting or quantifying the detection target substance based on the detected first fluorescence and the detected second fluorescence.

2. A biological molecule detecting apparatus for use in the biological molecule detecting method defined in claim 1, comprising:
    a light source that emits the excitation light having the component which is linearly polarized in a specific direction that excites the fluorescent molecules;
    a light receiving section that detects the fluorescence emitted by the fluorescent molecules;
    orientation control means for switching the orientations of the first complex and the second complex within the solution in at least two directions; and
    a calculating section that detects or quantifies the detection target substance by calculating the intensity of the second fluorescence from temporal changes in the intensity of the fluorescence emitted by the fluorescent molecules accompanying the switching of the orientations of the first complex and the second complex.

3. A biological molecule detecting apparatus as defined in claim 2, wherein:
    the orientation control means switches the orientation of the first complex and the second complex between an orientation in a first direction in which the longitudinal directions of the orienting labels and the specific are parallel, and an orientation in a second direction in which the longitudinal direction of the orienting labels and the specific direction are perpendicular.

4. A biological molecule detecting apparatus as defined in claim 2, wherein:
    the orientation control means switches the orientation of the first complex and the second complex at predetermined temporal intervals; and
    the calculating section calculates an arithmetic mean of a plurality of intensities of the second fluorescence, obtained by the orientations of the first complex and the second complex being switched a plurality of times, and detects or quantifies the detection target substance based on the arithmetic mean of the fluorescent intensities.

5. A biological molecule detecting apparatus as defined in claim 3, wherein:
    the orientation control means switches the orientation of the first complex and the second complex at predetermined temporal intervals; and
    the calculating section calculates an arithmetic mean of a plurality of intensities of the second fluorescence, obtained by the orientations of the first complex and the second complex being switched a plurality of times, and detects or quantifies the detection target substance based on the arithmetic mean of the fluorescent intensities.

6. A biological molecule detecting apparatus as defined in claim 4, wherein:
    the predetermined temporal intervals are determined based on one of the mass and the volume of the detection target substance, one of the mass and the volume of the specific binding substance, one of the mass and the volume of the orienting label, one of the mass and the volume of the fluorescent molecules, and the intensity of orientation control exerted by the orientation control means.

7. A biological molecule detecting apparatus as defined in claim 2, wherein:
    the orientation control means is equipped with an orientation controlling light source that emits linearly polarized light, and controls the orientations of the first complex and the second complex by emitting the linearly polarized light onto the solution.

8. A biological molecule detecting apparatus as defined in claim 3, wherein:
    the orientation control means is equipped with an orientation controlling light source that emits linearly polarized light, and controls the orientations of the first complex and the second complex by emitting the linearly polarized light onto the solution.

9. A biological molecule detecting apparatus as defined in claim 7, wherein:
    the orientation control means is equipped with a wavelength plate that changes the vibration direction of the linearly polarized light, and switches the orientations of the first complex and the second complex by switching the vibration direction of the linearly polarized light employing the wavelength plate.

10. A biological molecule detecting apparatus as defined in claim 7, wherein:
the orientation controlling light source emits the linearly polarized light onto the solution from a plurality of positions.

11. A biological molecule detecting apparatus as defined in claim 7, wherein:
the solution is held in a solution holding portion having a flat surface at least at a portion thereof.

12. A biological molecule detecting apparatus as defined in claim 11, wherein:
the orientation controlling light source emits the linearly polarized light in a direction that passes through the solution and exits the flat surface of the solution holding portion such that the linearly polarized light is focused at an interface between the solution and the flat surface.

13. A biological molecule detecting apparatus as defined in claim 2, wherein:
the calculating section calculates the intensity of the second fluorescence by utilizing the fact that there are differences in the temporal changes in the intensity of fluorescence emitted by the first complex and the temporal changes in the intensity of fluorescence emitted by the second complex during the switch of the orientation by the orientation control means from a first direction to a second direction.

14. A biological molecule detecting apparatus as defined in claim 3, wherein:
the calculating section calculates the intensity of the second fluorescence by utilizing the fact that there are differences in the temporal changes in the intensity of fluorescence emitted by the first complex and the temporal changes in the intensity of fluorescence emitted by the second complex during the switch of the orientation by the orientation control means from a first direction to a second direction.

15. A biological molecule detecting apparatus as defined in claim 4, wherein:
the calculating section calculates the intensity of the second fluorescence by utilizing the fact that there are differences in the temporal changes in the intensity of fluorescence emitted by the first complex and the temporal changes in the intensity of fluorescence emitted by the second complex during the switch of the orientation by the orientation control means from a first direction to a second direction.

16. A biological molecule detecting apparatus as defined in claim 2, wherein:
the light receiving section is equipped with spectral means for spectrally separating light.

17. A biological molecule detecting apparatus as defined in claim 16, wherein:
the spectral means is a plurality of filters having different properties; and
the light receiving section switches a filter to be employed from among the plurality of filters according to the wavelength of the fluorescence emitted by the fluorescent molecules.

* * * * *